US012138394B2

(12) United States Patent
Mühlbauer et al.

(10) Patent No.: US 12,138,394 B2
(45) Date of Patent: *Nov. 12, 2024

(54) HME DEVICE FOR USE IN A BREATHING CIRCUIT OF A VENTILATION SYSTEM

(71) Applicant: Drägerwerk AG & Co. KGaA, Lübeck (DE)

(72) Inventors: Pierre Mühlbauer, Lübeck (DE); Stefan Kolk, Groß Grönau (DE); Manuel Altherr, Steinwenden (DE); Xenia Subenko, Neuenkirchen-Vörden (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 113 days.

This patent is subject to a terminal disclaimer.

(21) Appl. No.: 17/728,428

(22) Filed: Apr. 25, 2022

(65) Prior Publication Data

US 2022/0241543 A1 Aug. 4, 2022

Related U.S. Application Data

(62) Division of application No. 16/521,312, filed on Jul. 24, 2019, now Pat. No. 11,351,327, which is a division of application No. 15/427,411, filed on Feb. 8, 2017, now abandoned.

(30) Foreign Application Priority Data

Feb. 9, 2016 (DE) ..................... 10 2016 001 408.3

(51) Int. Cl.

| | |
|---|---|
| ***A61M 16/10*** | (2006.01) |
| ***A61M 16/08*** | (2006.01) |
| ***A61M 16/20*** | (2006.01) |

(52) U.S. Cl.

CPC .... *A61M 16/1045* (2013.01); *A61M 16/0891* (2014.02); *A61M 16/201* (2014.02)

(58) Field of Classification Search

CPC .......... A61M 16/1045; A61M 16/0891; A61M 16/201; A61M 16/10; A61M 16/1075; A61M 16/14; A61M 2210/1025

See application file for complete search history.

(56) References Cited

U.S. PATENT DOCUMENTS

| | | | |
|---|---|---|---|
| 11,351,327 B2 * | 6/2022 | Mühlbauer ....... | A61M 16/1045 |
| 2004/0084046 A1 * | 5/2004 | Halperin ........... | A61M 16/1045 128/201.13 |
| 2004/0123974 A1 * | 7/2004 | Marler .............. | A61M 16/1055 165/9.4 |

* cited by examiner

*Primary Examiner* — Tasnim Mehjabin Ahmed

(74) *Attorney, Agent, or Firm* — McGlew and Tuttle, P.C.

(57) ABSTRACT

An HME device, used in a closed breathing circuit of a ventilation system, has a housing with an inlet opening and with an outlet opening, an HME chamber (50*a;* 50*b;* 50*c;* 50*d;* 50*e;* 50*f;* 50*g;* 50*h;* 50*i*) arranged between the inlet opening and the outlet opening for receiving an HME medium and a switching mechanism (70*a;* 70*b;* 70*c;* 70*d;* 70*e;* 70*f;* 70*g;* 70*h;* 70*i*). The HME device can be switched over between an HME mode (M1), in which an HME fluid passage is provided from the inlet opening through the HME chamber to the outlet opening, and a bypass mode (M2), in which a fluid bypass passage is provided from the inlet opening past the HME chamber through a bypass channel (80*a;* 80*b;* 80*d;* 80*e;* 80*f;* 80*h*) in the housing to the outlet opening. The bypass channel is blocked with respect to the HME chamber in the bypass mode (M2).

20 Claims, 16 Drawing Sheets

HME DEVICE FOR USE IN A BREATHING CIRCUIT OF A VENTILATION SYSTEM

CROSS REFERENCE TO RELATED APPLICATIONS

This application is a divisional of, and claims the benefit of priority under 35 U.S.C. § 120 of, U.S. patent application Ser. No. 16/521,312 filed Jul. 24, 2019, which is a divisional of U.S. patent application Ser. No. 15/427,411 filed Feb. 8, 2017, which claims the benefit of priority under 35 U.S.C. § 119 of German Application 10 2016 001 408.3 filed Feb. 9, 2016, the entire contents of each application are incorporated herein by reference.

FIELD OF THE INVENTION

The present invention pertains to an HME device (heat and moisture exchanger or humidification moisture exchanger) for use in a closed breathing circuit of a ventilation system. The HME device has a housing with an inlet opening and with an outlet opening as well as an HME chamber arranged between the inlet opening and the outlet opening for receiving an HME medium. Such an HME device can be switched over between an HME mode, in which the passage of a fluid from the inlet opening through the HME chamber to the outlet opening is provided, and a bypass mode, in which the passage of fluid is provided from the inlet opening past the HME chamber through a bypass channel to the outlet opening.

BACKGROUND OF THE INVENTION

Such HME devices are known in the state of the art. For example, U.S. Pat. No. 7,594,509 B2 shows an HME device, in which a first housing half with an inlet opening can be rotated relative to a second housing half with an outlet opening in order to switch over between an HME mode and a bypass mode. A similar principle of operation appears from DE 601 06 837 T2, U.S. Pat. No. 7,347,203 B2 as well as U.S. Pat. No. 6,976,488 B2. U.S. Pat. No. 6,976,488 B2 shows, furthermore, a solution in which an HME medium can be compressed by a plunger. However, liquid, which is located within the HME medium, can escape as a result and reach a respiratory system of a connected patient. In addition, the potentially contaminated plunger represents a risk of infection for a patient. In addition, it is problematic in all the above-mentioned HME devices that a contact may occur between a drug aerosol and the HME medium in the bypass mode in the phase of inhalation and in the phase of exhalation, as a result of which the flow resistance of the HME device may increase.

SUMMARY OF THE INVENTION

An object of the present invention is to take the above-described drawbacks at least partly into account in HME devices for use in a closed breathing circuit of a ventilation system. In particular, an object of the present invention is to provide a cost-effective HME device for use in a closed breathing circuit of a ventilation system, by means of which switching over is possible between an HME mode and a bypass mode in a simple and reliable manner and a contact between the drug aerosol and the HME medium can reliably be prevented at the same time.

According to a first aspect of the present invention, an HME device for use in a closed breathing circuit of a ventilation system is provided. The HME device has a housing with an inlet opening, with an outlet opening as well as with an HME chamber arranged between the inlet opening and the outlet opening for receiving an HME medium. The HME device has, further, a switching mechanism, by which the HME device can be switched over between an HME mode, in which the passage of an HME fluid is provided from the inlet opening through the HME chamber to the outlet opening, and a bypass mode, in which a fluid bypass passage is provided from the inlet opening past the HME chamber through a bypass channel in the housing to the outlet opening. The bypass channel is blocked according to the present invention against the HME chamber in the bypass mode.

The fact that the bypass channel of the HME device is blocked against the HME chamber in the bypass mode shall mean here that the bypass chamber is blocked or closed in an especially sealing manner against the HME chamber in the bypass mode, i.e., the bypass channel and the HME chamber are separated from one another in terms of fluid flow in the bypass mode, and no or essentially no fluid contact is therefore possible in the bypass mode between the bypass channel and the HME chamber and no fluidic interaction or essentially no fluidic interaction may occur between the bypass channel and the HME chamber. The HME chamber or an HME medium located in it is separated now on both sides from the bypass channel as well as from the inlet opening and the outlet opening. The HME chamber is preferably closed in the bypass mode, i.e., it is fluidically separated or essentially separated from the area surrounding the HME chamber. Due to the separation of the HME chamber from the bypass channel according to the present invention in the bypass mode, it is possible, for example, to prevent a drug aerosol from coming into contact with the HME medium during the atomization of a drug.

The HME chamber is not limited to a chamber with a single chamber space. It is possible, in particular, that the HME chamber has a chamber with a plurality of HME chamber sections. The HME chamber may, furthermore, be configured as a closed or opened chamber. The HME chamber can preferably be switched over between a closed state and an opened state. The HME chamber is especially preferably opened in the HME mode and, as was already shown above, closed, preferably completely, at least against the bypass channel in the bypass mode. The HME chamber is opened in the HME mode such that the passage of HME fluid from the inlet opening through the HME chamber to the outlet opening can be provided.

In the sense of the present invention, the inlet opening may also be an outlet opening and the outlet opening may also be an inlet opening. The concretization of the inlet opening and the outlet opening shall only be used in the embodiments for a simpler and clearer representation of the present invention.

An HME device is defined, in principle, as a heat and moisture exchanger known in the state of the art for ventilation systems. A fluid passage is defined according to the present invention especially as a possibility of fluid passage in a fluid channel, through which a fluid, for example, a drug aerosol or breathing air of a patient can flow. The switching mechanism is defined as a generic term for the elements of the HME device that are in a functional relationship and that are necessary for switching over between the HME mode and the bypass mode.

According to a variant of the present invention, the housing has an inlet-side housing half with the inlet opening and an outlet-side housing half with the outlet opening, the HME chamber being formed by an inner wall section of the inlet-side housing half and by an inner wall section of the outlet-side housing half, and the inlet-side housing half and the outlet-side housing half being arranged rotatably in relation to one another to block and open the bypass channel. Due to the housing halves being mounted and arranged rotatably in relation to one another, the HME device can be switched over between the HME mode and the bypass mode in an especially simple manner. In addition, this makes possible a one-hand operation, in which, for example, only one of the two housing halves is rotated by a user against the other of the two housing halves. The two housing halves are preferably arranged rotatably relative to one another about the same axis of rotation. It may be advantageous in this connection if only one of the two housing halves is arranged rotatably in relation to the other of the two housing halves. However, both housing halves may also be arranged rotatably relative to one another about an axis of rotation. In the case in which only one of the two housing halves is arranged rotatably in relation to the other of the two housing halves, it may, further, be advantageous if the inlet opening corresponds to a passage opening in a fluid inlet channel and the outlet opening corresponds to a passage opening in a fluid outlet channel, wherein a rotatable housing half is arranged rotatably relative to the fluid inlet channel of the other housing half as well as to the fluid outlet channel. It can be achieved as a result that when rotating one housing half or when switching over between the HME mode and the bypass mode, neither the fluid inlet channel nor the fluid outlet channel is rotated. As a result, connection tubes or corresponding channels can be fastened to the fluid inlet channel and/or the fluid outlet channel especially tightly or in an especially fluid-tight manner. The HME device preferably has a turning handle, which is arranged on at least one of the two housing halves in order to rotate the housing halves more easily in relation to one another. Due to the rotation of the housing halves, the corresponding inner wall sections of the housing halves are rotated, as a result of which the HME chamber is correspondingly opened or closed or blocked. The inlet-side housing half may, of course, also be an outlet-side housing half in the sense of the present invention and the outlet-side housing half may, of course, also be an inlet-side housing half in the sense of the present invention. All inlet elements according to the present invention may also be defined as being outlet elements and all outlet elements according to the present invention may also be defined as inlet elements.

Further, it is possible according to the present invention that the inlet-side housing half has first inlet holes, second inlet holes, inlet diaphragms and inlet diaphragm passages between the inlet diaphragms and the outlet-side housing half has outlet holes and outlet diaphragms, wherein the first inlet holes and the inlet diaphragm passages are covered by the outlet diaphragms in the bypass mode and the second inlet holes are arranged at least partly flush with the outlet holes. Due to the coverage of the first inlet holes and of the inlet diaphragm passages by the outlet diaphragms or through same, it is possible to reliably prevent a contact between the drug aerosol and the HME medium in the bypass mode and to block the bypass channel against the HME chamber. Due to the two inlet holes being arranged at least partly flush with the outlet holes, a fluid bypass passage from the inlet opening past the HME chamber to the outlet opening can be guaranteed. The first inlet holes are preferably arranged uniformly around an axis of rotation. The second inlet holes are preferably also arranged uniformly around an axis of rotation. The first inlet holes and the second inlet holes are especially arranged around the same axis of rotation and are located at spaced locations from one another in the longitudinal direction of the axis of rotation, being especially located at spaced locations from one another over the full circumference in the longitudinal direction of the axis of rotation. The first and second passage holes are, in addition, arranged and configured offset in relation to one another preferably in the circumferential direction of the axis of rotation, i.e., the first and second passage holes are not preferably arranged flush or essentially flush with one another along a straight line or plane that is parallel or essentially parallel to the axis of rotation. However, the first inlet holes are arranged flush with the inlet diaphragm passages in at least some sections along the straight line or plane that is parallel or essentially parallel to the axis of rotation. The circumstance that the inlet holes and the inlet diaphragm passages are covered by the outlet diaphragms means in the sense of the present invention that the outlet diaphragms cover, seal and/or close the inlet holes and the inlet diaphragm passages in a fluid-tight manner. According to this variant, a fluid bypass passage is provided in the bypass mode from the inlet opening past the HME chamber through the bypass channel and through the second inlet holes and the outlet holes to the outlet opening. A fluid bypass passage is correspondingly also provided from the outlet opening past the HME chamber through the bypass channel and through the outlet holes and the second inlet holes to the inlet opening. In the HME mode, i.e., after rotation of the first housing half in relation to the second housing half, the second inlet holes are opened by wall sections between the outlet holes and the outlet holes are covered by wall sections between the second inlet holes and the first inlet holes as well as the inlet diaphragm passages, i.e., they are no longer covered by the outlet diaphragms. As a result, an HME fluid passage is provided from the inlet opening through the first inlet holes, the HME chamber, the inlet diaphragm passages to the outlet opening. At the same time, an HME fluid passage is correspondingly provided from the outlet opening through the inlet diaphragm passages, the HME chamber and the first inlet holes to the inlet opening.

In addition, it is possible according to the present invention that a bistable holding mechanism, by which the two housing halves can be held in defined or predefined, different positions or end positions in relation to one another, is formed on the inlet-side housing half and/or on the outlet-side housing half Intermediate switching positions between the HME mode and the bypass mode can reliably be prevented thereby. A bistable holding mechanism is defined here as a holding mechanism that can assume two possible states and can change over into the other state by an external force or input only. The bistable holding mechanism has, for example, a convex projection on an outer wall section of a housing half, via which a grip element of the other housing half can be displaced in at least some sections, especially in the area of the greatest arch of the convex projection, based on a surface friction between the convex projection and the grip element. When the grip element is moved over the outer contour of the convex projection, a restoring force is generated, which acts up to the point of the greatest deflection. If the grip element is moved beyond this point over the described contour, a force acts in the direction of a switchover motion between the HME mode and the bypass mode. Only one of the two modes, i.e., the HME mode or the bypass mode, can thus be active, without intermediate switching states being able to be reached. A stop each is provided for the grip element in the respective position or end position in order to hold and/or lock the grip element securely in the particular end position. The bistable holding mechanism may correspondingly also be configured as a bistable locking mechanism.

According to another aspect of the present invention, the HME chamber is configured by an inner wall section of the housing and an outer wall mechanism of a displacing device of the HME device for displacing the HME medium, the displacing device being arranged movably for blocking the bypass channel in the bypass mode in relation to the HME chamber. An HME device of an especially simple design, in which a contact between drug aerosol and HME medium can nevertheless reliably be prevented in the bypass mode, can be provided due to the movably arranged partition. The displacing device is preferably configured in the form of a partition and it displaces the HME medium by compressing said medium and correspondingly allows it to recover again, i.e., a displacement of the HME medium is defined here as a displacement of the HME medium or of a part of the HME medium in at least some sections.

In addition, it is possible according to the present invention that the outer wall section is configured as a wall section that is elastically deformable at least partly or in at least some sections for displacing the HME medium and/or for blocking the bypass channel in the bypass mode in relation to the HME chamber. The outer wall section is defined here especially as a wall section with an outer wall surface. In such an embodiment variant, the outer wall section can be moved and/or deformed by a separate actuating device or directly. The outer wall section or the displacing device is preferably configured such that it is elastically deformable at least in the area in which it can come into direct contact with an HME medium in the HME chamber. The displacing device may have here, for example, a plate-shaped partition section, which is arranged in a bent state in the housing. More precisely, the plate-shaped partition section may be in contact with an inner wall section or an inner wall surface of the housing in an HME mode in an HME position. The plate-shaped partition section may be arranged and configured here such that in case of a switchover from the HME mode into the bypass mode, it can be moved from the HME position into a bypass position, for which the plate-shaped partition section is moved and/or deformed from the one inner wall section in the direction of an opposite inner wall section and out of the HME fluid passage.

In addition, it may be advantageous according to the present invention if the displacing device has two plate-shaped partition sections for separating the HME medium in at least some sections, wherein at least one of the two plate-shaped partition sections are arranged movably for displacing the HME medium and/or for blocking the bypass channel in the bypass mode against the HME chamber. Compared to one embodiment variant, in which the displacing device has only a single plate-shaped partition section, only a relatively slight motion and/or deformation of the partition section is necessary in case of the movably arranged partition section to switch over between the HME mode and the bypass mode. Further, it is advantageous here that the HME medium must be displaced and/or deformed only correspondingly slightly.

In addition, it may be advantageous within the framework of the present invention if at least one of the two plate-shaped partition sections for displacing the HME medium and/or for blocking the bypass channel in the bypass mode against the HME chamber is configured as an at least partly elastically deformable partition section. The elastically deformable partition section is preferably configured as an elastically deformable partition section at least in the area in which it can or does come into direct contact with an HME medium in the HME chamber. A switchover between the HME mode and the bypass mode is possible in an especially simple manner especially due to the combination of a stationary plate-shaped partition section and an at least partly elastically deformably configured partition section, because only the at least partly elastically deformable partition section must be deformed for the switchover.

It is possible according to a variant of the present invention that at least one of the two plate-shaped partition sections for displacing the HME medium and/or for blocking the bypass channel in the bypass mode against the HME chamber is arranged movably relative to the other plate-shaped partition section. Switchover is likewise possible in an especially simple manner between the HME mode and the bypass mode due to the combination of a stationary plate-shaped partition section and a movably arranged and/or configured partition section, because only the movably arranged partition section must be moved for the switchover.

In addition, it may be advantageous within the framework of the present invention if the two plate-shaped partition sections are arranged in the HME mode such that they are bent in the same first direction and at least one of the two plate-shaped partition sections for displacing the HME medium and/or for blocking the bypass channel in the bypass mode against the HME chamber is configured as a partition section deformable elastically in a second direction, which is opposite the first direction. It can be ensured hereby that the freest possible and most obstacle-free HME fluid passage possible is established through the HME medium in the HME mode. In addition, it is possible as a result to form a bypass channel for the bypass mode in an especially simple manner, namely by deforming the at least one plate-shaped partition section in the second direction.

In addition, it is possible according to the present invention that the displacing device or at least one of the two plate-shaped partition sections is arranged and configured elastically deformably such that the displacing device or the at least one of the two plate-shaped partition sections is deformable in a bistable manner, especially due to a residual stress of the displacing device of the at least one of the two plate-shaped partition sections, into a second HME end position or into a bypass end position. As a result, intermediate switching states between the HME mode and the bypass mode can reliably be prevented. The displacing device or the at least one of the two plate-shaped partition sections are arranged here in the housing preferably under a prestress. In addition, it is conceivable within the framework of the present invention that the displacing device or at least one of the two plate-shaped partition sections has a shape memory alloy, which is deformable such that the displacing device or at least one of the two plate-shaped partition sections is correspondingly deformable into the respective end position.

Another advantage may be that the displacing device is fixed in the housing at at least one point. A defined deflection and/or deformation of the displacing device can be facilitated hereby. It is especially preferred in this connection if the displacing device is fixed in the housing at two or four points. The displacing device is mounted here in the housing movably or pivotably in at least some sections about an axis of rotation or about two axes of rotation, i.e., the displacing device is fixed in the housing in the area of the axes of rotation or on corresponding shafts such that only a rotary motion but no translatory motion of the displacing device or of a section of the displacing device is possible. The displacing device can be moved and/or deformed hereby via a lever in an especially simple manner. This facilitates the desired one-hand actuation of the HME device according to the present invention.

In addition, it is possible according to the present invention that at least one manual actuating device is arranged for moving or elastically deforming the displacing device. The manual actuating device is defined in the sense of the present invention as an adjusting element, via which a user can move or elastically deform the displacing device by direct manual actuation.

It is, further, advantageous according to the present invention if the manual actuating device is connected to the displacing device, especially to one of the two plate-shaped partition sections and is especially configured monolithically with the displacing device. A reliable and precise displacement and/or deformation of the HME medium can be achieved due to the permanent connection between the displacing device and the manual actuating device. A monolithic or one-piece configuration of the displacing device with the manual actuating device simplifies the manufacturing process for manufacturing the HME device and leads to correspondingly low manufacturing costs.

In addition, it may be advantageous within the framework of the present invention if the manual actuating device has a lifting and rotating mechanism actuatable by pressing for moving and/or elastically deforming the displacing device, especially at least one of the two plate-shaped partition sections. The lifting and rotating mechanism is preferably configured as a bistable switching mechanism, i.e., the lifting and rotating mechanism according to the present invention can move and/or displace the displacing device or the at least one of the two plate-shaped partition sections into two possible end positions. More precisely, the lifting and rotating mechanism is configured such that the displacing device or the at least one of the two plate-shaped partition sections is moved into a first end position by a first pressure actuation of the lifting and rotating mechanism and the displacing device or the at least one of the two plate-shaped partition sections is moved into a second end position from the first end position by a second pressure actuation of the lifting and rotating mechanism. The lifting and rotating mechanism is preferably configured here in the form of a "retractable ballpoint pen mechanism" and shall not therefore be explained here in more detail. Intermediate switching states between the HME mode and the bypass mode can reliably be prevented by providing such a lifting and rotating mechanism.

In a variant of the present invention, the two partition sections have an outer wall surface and an inner wall surface each, wherein the outer wall surfaces correspond to the outer wall section and the inner wall surfaces correspond to an inner wall section of the bypass channel, i.e., the partition sections may form both a part of the HME chamber and a part of the bypass channel. An especially material-saving and hence also correspondingly cost-effective HME device can be provided hereby. The inner wall surfaces of the partition sections are located directly on one another and at one another in the HME mode. It is only for the bypass mode that the inner wall surfaces of the partition sections are arranged at spaced locations from one another such that they can form a part of the bypass channel. The circumstance that the outer wall surfaces correspond to the outer wall section and the inner wall surfaces correspond to the inner wall section means that the outer wall surfaces correspond to the outer wall section in at least some sections and the inner wall surfaces correspond to the inner wall section in at least some sections or are configured as same.

According to another aspect of the present invention, the displacing device has a stationary separating device and a movable separating device, wherein the movable separating device is arranged pivotably about an axis of rotation relative to the stationary separating device. As a result, the switchover between the HME mode and the bypass mode can be embodied in an especially simple manner. The movable separating device is preferably arranged fully pivotably. The movable separating device may be mounted pivotably in the housing at an inner wall section of the housing or at a frame element in the housing. The stationary separating device may likewise be fastened to an inner wall section of the housing or to a frame element in the housing. The frame element may be configured, for example, as an HME storage frame, which is provided in the housing for receiving the HME medium and is preferably fixed or fastened in the housing. The HME storage frame may have, further, an outer circumferential wall section, which is fastened in at least some sections on an inner wall section of the housing. To increase the rigidity, the HME storage frame may have struts. In a preferred embodiment variant, the movable separating device and/or the stationary separating device are fixed each at one of the struts and mounted pivotably. The HME medium can be displaced or compressed and moved in the process out of or into the fluid bypass passage by pivoting the movable separating device.

According to a variant of the present invention, the stationary separating device and the movable separating device may have each an outer wall surface and an inner wall surface. wherein the outer wall surfaces correspond to the outer wall section and the inner wall surfaces correspond to an inner wall section of the bypass channel. As a result, an especially material-saving and hence also correspondingly cost-effective HME device is provided. The inner wall surfaces of the separating device lie on one another in at least some sections in the HME mode, and the inner wall surfaces are located at spaced locations from one another to form a bypass channel in the HME mode.

In addition, it is possible according to the present invention that at least one manual actuating device is arranged outside the housing displaceably in the circumferential direction of the housing for pivoting the movable separating device. As a result, the movable separating device can be adjusted into the desired position in a simple manner and it can thus be switched over between the HME mode and the bypass mode in a correspondingly simple manner.

It is advantageous here if the manual actuating device is permanently connected to the movable partition and is configured especially monolithically with the movable separating device. Due to the permanent connection between the movable separating device and the manual actuating device, reliable and accurate motion of the movable separating device and hence a correspondingly reliable and accurate switchover between the HME mode and the bypass mode can be guaranteed. If the movable separating device and the manual actuating device are configured as a monolithic component, this simplifies the manufacturing process for the HME device and the cost can correspondingly be reduced.

According to another aspect of the present invention, the HME chamber is configured by an inner wall section of the inlet-side housing half, by an inner wall section of the outlet-side housing half and by an outer wall section of a displacing device of the HME device for displacing the HME medium, the displacing device having a first separating device and a second separating device for blocking the bypass channel in the bypass mode against the HME chamber, the first separating device and the second separating device being arranged pivotably about an axis of rotation in relation to one another, and the first separating device being in functional connection with one of the inlet-side housing half and of the outlet-side housing half and the second separating device being in functional connection with the other of the inlet-side housing half and of the outlet-side housing half. It is possible as a result to achieve a simple switchover between the HME mode and the bypass mode by rotating the housing halves. The housing halves do not have to be rotated completely against one another. It is decisive that the HME medium is sufficiently compressed by the first separating device and the second separating device, i.e., it is pressed apart such that it is arranged outside the fluid bypass passage from the inlet opening to the outlet opening. For example, a rotation of the housing halves in relation to one another by less than 60°, preferably by a value between 30° and 45°, is sufficient here.

It is possible according to a variant of the present invention that the first separating device and the second separating device have an outer wall surface and an inner wall surface each, wherein the outer wall surfaces correspond to the outer wall section and the inner wall surfaces correspond to an inner wall section of the bypass channel. An especially material-saving and correspondingly cost-effective HME device is created hereby. The inner wall surfaces lie on one another in the HME mode. The inner wall surfaces are arranged at spaced locations from one another in the bypass mode to form the bypass channel and are arranged at correspondingly spaced locations from one another to form the bypass channel.

In addition, it is possible according to the present invention that the first separating device is fastened to one of the inlet-side housing half and of the outlet-side housing half and is configured especially monolithically with the corresponding housing half, and the second separating device is fastened to the other of the inlet-side housing half and of the outlet-side housing half, and is configured especially monolithically with the corresponding housing half Due to the separating device being fastened according to the present invention to the housing halves, an especially reliable and defined displacement or shifting of the HME medium in the housing and in the HME chamber can be guaranteed. If the separating device and the housing halves are each configured as a monolithic component, this simplifies the manufacturing process for the HME device and the costs can correspondingly be reduced.

It is possible according to another aspect of the present invention that a hollow section is arranged in the housing rotatably about an axis of rotation and an inner wall section of the HME chamber corresponds to an inner wall section of the hollow section and a section of the bypass channel can be established between a first outer wall section of the hollow section and a first inner wall section of the housing, and the first outer wall section of the hollow section especially corresponds to an inner wall section of the bypass channel. The circumstance that the inner wall section of the HME chamber corresponds to the inner wall section of the hollow section means that the inner wall section of the HME chamber corresponds to the inner wall section of the hollow section and is configured as same. The circumstance that the first outer wall section of the hollow section corresponds to the inner wall section of the bypass channel means that the first outer wall section of the hollow section corresponds to the inner wall section of the bypass channel and is configured as same. The HME medium does not have to be displaced or deformed in the hollow section according to the present invention in order to be moved out of the HME fluid channel. It is thus possible to switch over between the HME mode and the bypass mode with a correspondingly low resistance and with the expenditure of a correspondingly weak force. Due to the fact that a section of the bypass channel can be established between the first outer wall section of the hollow section and the first inner wall section of the housing and that, in particular, the first outer wall section of the hollow section corresponds to the inner wall section of the bypass channel, an especially material-saving and hence correspondingly cost-effective HME device can, in addition, be provided.

It is possible according to a variant of the present invention that a second outer wall section of the hollow section is flush-integrated or essentially flush-integrated in contact with a second inner wall section of the housing. As a result, the HME device can be provided as an especially space-saving device. The second outer wall section is preferably arranged now flush-integrated at the second inner wall section such that the second outer wall section and the second inner wall section can be moved or rotated in relation to one another without great friction. It may be advantageous for this that the second outer wall section as well as the second inner wall section are configured in at least some sections as slide bearings, with slide bearing properties or with a surface roughness for slide bearing properties.

Moreover, it is possible within the framework of the present invention that the HME chamber is formed by an inner wall section of the hollow section and by an inner wall section of the housing. The HME device can thus be provided in an especially space-saving and hence correspondingly cost-effective manner as well.

It is also advantageous in this connection if the housing has a housing window, through which the hollow section is exposed section by section to the outside. It is easy as a result for a user of the HME device to rotate the hollow section, which is arranged essentially in the housing by a manual actuation of the hollow section for switching over between the HME mode and the bypass mode. It is especially advantageous in this case if an outer wall section or an outer wall surface of the hollow section, which can be rotated, visibly from the outside, into the housing window, has an HME marking for the bypass mode, for example, "bypass" or "aerosol." The markings may be arranged on the outer wall section of the hollow section such that the HME marking can be seen on the housing window in the HME mode and the bypass marking can be seen on the housing window in the bypass mode. A user can thus recognize immediately whether the HME device is currently in the HME mode or in the bypass mode.

According to another aspect of the present invention, the housing has a fluid inlet channel and a fluid outlet channel, the fluid inlet channel being connected to a first fluid switchover channel and the outlet channel being connected to a second fluid switchover channel, the first fluid switchover channel extending at right angles to the fluid inlet channel and the second fluid switchover channel extending at right angles to the fluid outlet channel, and the fluid inlet channel, the first fluid switchover channel, the second fluid switchover channel and the fluid outlet channel corresponding, in at least some sections, to the bypass channel in the bypass mode. This represents a further alternative embodiment variant, by means of which switchover is possible between the HME mode and the bypass mode in a simple and reliable manner and a contact between drug aerosol and HME medium can at the same time reliably be prevented.

The fluid inlet channel and the fluid outlet channel are preferably configured as separate or not monolithically connected components. The first fluid switchover channel preferably extends at right angles to the fluid inlet channel such that an angle between 100° and 170°, especially preferably between 120° and 150° is formed between the first fluid switchover channel and the fluid inlet channel. The second fluid switchover channel preferably extends at right angles to the fluid outlet channel such that an angle between 100° and 170°, especially preferably 120° and 150° is formed between the second fluid switchover channel and the fluid outlet channel. The space available in the housing can be utilized especially advantageously as a result. The first fluid switchover channel and the second fluid switchover channel are preferably configured here such that there is a flush connection between the first fluid switchover channel and the second fluid switchover channel in the bypass mode, especially between a ring-shaped end face of the first fluid channel and a ring-shaped end face of the second fluid channel, in at least some sections, i.e., the first fluid switchover channel and the second fluid switchover channel and the respective end faces thereof abut against each other in a flush-integrated manner, especially in a fluid-tight flush-integrated manner.

According to a variant of the present invention, the first fluid switchover channel and the second fluid switchover channel are arranged, in at least some sections, in parallel or essentially in parallel to one another in the HME mode. Due to such an arrangement and configuration of the fluid switchover channels, the space available in the housing or in the HME chamber can be utilized especially advantageously. In addition, an especially uniform design of the HME device can be obtained hereby, as a result of which identical or at least very similar components can be used, which in turn leads to a simple and cost-effective manufacture of the HME device.

Moreover, it is conceivable according to the present invention that the HME medium is arranged in the HME chamber and the HME medium has a stepped passage channel, in which one of the fluid inlet channel and the fluid outlet channel is arranged displaceably and the other of the fluid inlet channel and of the fluid outlet channel is arranged, in at least some sections, circumferentially in a positive-locking or flush-integrated manner with the HME medium. It can be ensured hereby that the HME medium is held in a defined position when the fluid channel, which is arranged displaceably in the HME medium, is displaced or moved. To arrange the fluid inlet channel or the fluid outlet channel displaceably or movably in the HME medium, the HME medium has a C-shaped, essentially C-shaped recess or a recess bent or extending in the circumferential direction of the HME medium, in which the fluid inlet channel or the fluid outlet channel can move, without displacing or deforming the HME medium. The stepped passage channel is defined in the sense of the present invention as a passage opening in the HME medium, which is not configured as a continuous passage opening but is configured with a step or with an edge, i.e., with a step between an inlet opening and an outlet opening of this passage opening.

According to another aspect of the present invention, the housing has an inlet-side housing half and an outlet-side housing half, wherein an fluid inlet channel is arranged in the inlet-side housing half. The fluid inlet channel and the inlet-side housing half are arranged rotatably relative to one another, and the fluid inlet channel has an inlet opening, which corresponds to the inlet opening of the HME device, and a passage opening. The passage opening is directed into the HME chamber in the HME mode and into the bypass channel in the bypass mode. A further embodiment variant is provided hereby, by means of which an especially simple switchover is possible between the HME mode and the bypass mode. It is, in addition, possible due to the configuration according to the present invention to embody an especially material-saving and hence correspondingly cost-effective HME device. In particular, the inlet-side housing half is arranged according to the present invention rotatably in relation to the fluid inlet channel as well as to the outlet-side housing half. As a result, a user of this HME device is able to switch over between the HME mode and the bypass mode by rotating the inlet-side housing half in an especially simple manner. Due to the fact that only the inlet-side housing half is rotated during a switchover between the HME mode and the bypass mode, while the fluid inlet channel as well as the outlet-side housing half are not moved, fluid channels can be arranged in an especially rigid and fluid-tight manner at the fluid inlet channel and the outlet-side housing half. The fluid inlet channel protrudes according to the present invention into the inlet-side housing half in at least some sections and through the inlet-side housing half until it comes into contact with the outlet-side housing half, with which the fluid inlet channel is preferably in contact in at least some sections in a flush-integrated manner. Due to this coupling of the fluid inlet channel with the inlet-side housing half as well as with the outlet-side housing half in case of the above-described rotatable mounting at least of the inlet-side housing half, an HME device, which has an especially simple design and yet functions reliably, can be created. The passage opening described in connection with this embodiment is defined especially as an outlet-side opening in the fluid inlet channel. This opening is not limited here to a circular pipe opening. This passage opening may rather also have different opening sections or an opening area having any desired geometric shape.

According to a variant of the present invention, it is advantageous if the passage opening has a lateral opening section and a frontal opening section, the opening direction of the lateral opening section being directed at right angles to the opening direction of the inlet opening and/or of the frontal opening section. The lateral opening section and the frontal opening section may be separated here from one another by a web or another separating area or provided as sections of a single opening or passage opening. It is possible as a result that an HME fluid passage is provided from the inlet opening through the lateral opening section into the HME medium and from the HME medium through the frontal opening section farther through the outlet opening. If the inlet-side housing half is rotated now relative to the fluid inlet channel, i.e., if there is a switchover from the HME mode into the bypass mode, a fluid bypass passage is provided from the inlet opening through the lateral opening section into a bypass chamber and from the bypass chamber through the frontal opening section farther through the outlet opening. The bypass channel corresponds in this case to a channel section that is formed by the fluid inlet channel, the inlet-side housing half and the outlet-side housing half. It is especially advantageous in this connection if an HME chamber, which occupies at least 50%, preferably more than 70% of the volume or of an inner volume area of the inlet-side housing half, which area is defined by an inner wall section of the inlet-side housing half and an open area thereof, is formed in the inert-side housing half.

Further, it is possible according to the present invention that the fluid inlet channel has a wall section that is arranged, especially flush with the lateral opening section, in the fluid inlet channel in parallel to or essentially in parallel to the opening direction of the lateral opening section. As a result, a fluid passage or a corresponding fluid can advantageously be sent in the direction of the HME chamber or the bypass chamber through the lateral opening section. The wall section is preferably a monolithic component of the fluid inlet channel, but it may also be arranged as a separate component. The wall section is preferably configured at right angles, especially preferably mutually perpendicularly or essentially mutually perpendicularly to an inner wall section or an inner wall surface of the fluid inlet channel. As a result, an especially efficient bypass can be achieved from the fluid inlet channel in the direction of the HME chamber or from the bypass chamber.

Moreover, it is possible in the sense of the present invention that the wall section has a height that corresponds to at least half of the height, especially to the entire passage height of the fluid inlet channel at the site of the wall section. As a result, the fluid passage or a corresponding fluid can be sent especially effectively in the direction of the HME chamber or the bypass chamber. To reduce turbulent flows or to reduce flow resistances, the wall section may have, in at least some sections, a convex and/or concave wall surface, which sends a fluid flow from the inlet opening better in the direction of the HME chamber or the bypass chamber and prevents the fluid flow from impinging against the wall section with full force at right angles or in a mutually perpendicular direction.

According to another aspect of the present invention, an HME storage frame is arranged in the housing for storing the HME medium and the HME storage frame is mounted rotatably about an axis of rotation for switching over between the HME mode and the bypass mode, the HME storage frame having an outer ring section and a storage frame passage channel within the outer ring section, the HME chamber being formed by an inner wall section of the housing, by an inner wall section of the outer ring section and by an outer wall section of the storage frame passage channel, and an inner wall section of the storage frame passage channel corresponding to an inner wall section in the bypass mode. An additional embodiment variant is provided by this, by means of which an especially simple switchover is possible between the HME mode and the bypass mode. The storage frame passage channel is preferably configured as an inner ring section, i.e., is correspondingly ring-shaped, especially in the form of a closed ring. The outer ring section and the inner ring section or the storage frame passage channel are preferably connected to one another by connection struts, which are surrounded or can be enclosed by the HME medium. As a result, the storage frame passage channel can be held in a stable manner in the outer ring section. Both parts of the HME chamber and parts of the bypass channel are configured by the present HME storage frame. As a result, an especially material-saving and correspondingly cost-effective solution is obtained for providing the HME device according to the present invention. The storage frame passage channel is preferably arranged eccentrically in the outer ring section and/or in the hosing. As a result, the storage frame passage channel can be rotated out of the HME fluid passage or the fluid bypass passage in a simple manner by rotating the HME storage frame.

It is advantageous in a variant of the present invention if an outer wall section of the outer ring section is in contact with an inner wall section of the housing in a flush-integrated manner. As a result, the HME storage frame can be twisted or rotated in the housing about the axis of rotation especially reliably and at the same time with low resistance and it can make possible a correspondingly simple switchover between the HME mode and the bypass mode.

Further, it is possible according to the present invention that an outer wall section of the outer ring section is functionally connected through a housing window to an adjusting element arranged outside the housing, and the HME storage frame is rotatable about the axis of rotation by moving the adjusting element. As a result, the HME storage frame can be rotated about the axis of rotation in an especially simple manner and switched over in a correspondingly simple manner between the HME mode and the bypass mode. The housing window is preferably sealed or closed in a fluid-tight manner against the HME chamber.

In addition, it may be advantageous in the sense of the present invention if the adjusting element surrounds the housing in a ring-shaped manner in at least some sections. It is possible as a result that a user can easily grasp the adjusting element for switching over between the HME mode and the bypass mode in each position and can rotate the HME storage frame in a correspondingly simple and user-friendly manner. The outer wall section of the ring-shaped section of the adjusting element is preferably profiled, i.e., it is provided with recessed grips and/or projections. As a result, the adjusting element can also be grasped properly with, for example, wet hands, and the HME storage frame can rotate correspondingly well. The adjusting element is always connected here functionally to the HME storage frame.

Moreover, it is possible according to the present invention that the adjusting element is functionally connected by a projection from the outer wall section of the outer ring section to same outer wall section. An especially simple, cost-effective and at the same time reliable functional connection is established by such a functional connection between the adjusting element and the HME storage frame. The projection may mesh, for example, with a corresponding mount in the adjusting element or be received lockingly in same. Such a nondestructively detachable connection between the adjusting element and the HME storage frame has the further advantage that the adjusting element can easily be replaced by another adjusting element in case of wear.

Further measures improving the present invention appear from the following description of different exemplary embodiments of the present invention, which are schematically shown in the figures. All the features and/or advantages, including design details and arrangements in space, which appear from the claims, the description or the drawings, may be essential for the present invention both in themselves and in the different combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
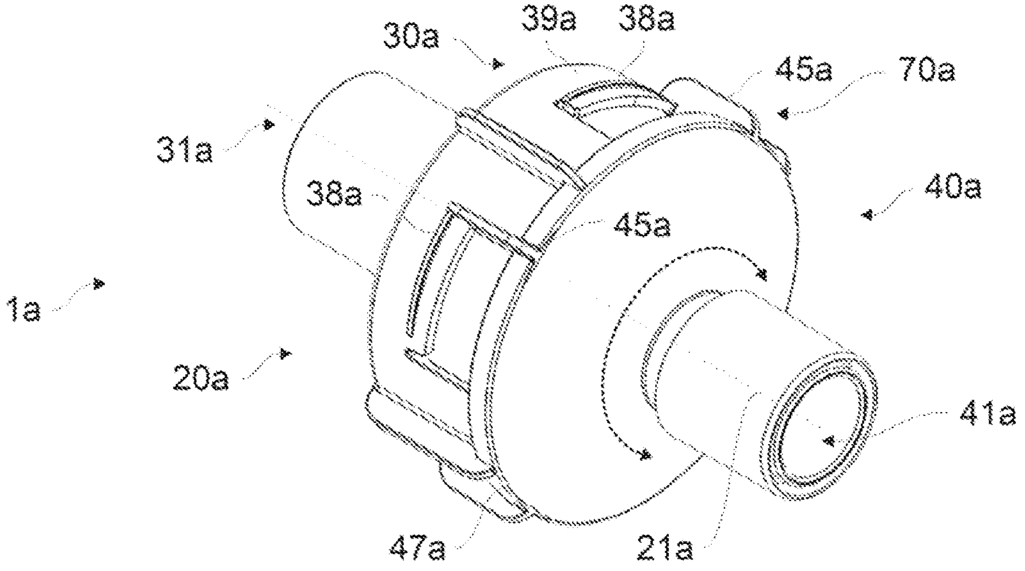
FIG. 1 is a perspective view of an HME device according to a first embodiment of the present invention.

Referring to the drawings, elements with the same function and mode of operation are always designated in FIGS. 1 through 35 by the same or similar reference numbers, which at times differ from one another only by embodiment-specific letters.

Different embodiments of an HME device 1*a*, 1*b*, 1*c*, 1*d*, 1*e*, 1*f*, 1g, 1*h*, 1*i* according to the present invention for use in a closed breathing circuit of a ventilation system are shown in FIGS. 1 through 35. The HME device 1*a*, 1*b*, 1*c*, 1*d*, 1*e*, 1*f*, 1g, 1*h*, 1*i* shown has a housing 20*a*, 20*b*, 20*c*, 20*d*, 20*e*, 20*f*, 20*g*, 20*h*, 20*i* with an inlet opening 31*a*, 31*b*, 31*c*, 31*d*, 31*e*, 31*f*, 31g, 31*h*, 31*i* and with an outlet opening 41*a*, 41*b*, 41*c*, 41*d*, 41*e*, 41*f*, 41g, 41*h*, 41*i*. Further, the HME device 1*a*, 1*b*, 1*c*, 1*d*, 1*e*, 1*f*, 1g, 1*h*, 1*i* has an HME chamber 50*a*, 50*b*, 50*c*, 50*d*, 50*e*, 50*f*, 50*g*, 50*h*, 50*i* arranged between the inlet opening 31*a*, 31*b*, 31*c*, 31*d*, 31*e*, 31*f*, 31g, 31*h*, 31*i* and the outlet opening 41*a*, 41*b*, 41*c*, 41*d*, 41*e*, 41*f*, 41g, 41*h*, 41*i* for receiving an HME medium 60*a*, 60*b*, 60*c*, 60*d*, 60*e*, 60*f*, 60*g*, 60*h*, 60*i*, which is configured here as an HME foam element. Moreover, the HME device 1*a*, 1*b*, 1*c*, 1*d*, 1*e*, 1*f*, 1g, 1*h*, 1*i* has a switching mechanism 70*a*, 70*b*, 70*c*, 70*d*, 70*e*, 70*f*, 70*g*, 70*h*, 70*i*, by which the HME device 1*a*, 1*b*, 1*c*, 1*d*, 1*e*, 1*f*, 1g, 1*h*, 1*i* can be switched between an HME mode M1, in which an HME fluid passage is provided from the inlet opening 31*a*, 31*b*, 31*c*, 31*d*, 31*e*, 31*f*, 31g, 31*h*, 31*i* through the HME chamber 50*a*, 50*b*, 50*c*, 50*d*, 50*e*, 50*f*, 50*g*, 50*h*, 50*i* to the outlet opening 41*a*, 41*b*, 41*c*, 41*d*, 41*e*, 41*f*, 41*g*, 41*h*, 41*i*, and a bypass mode M2, in which a fluid bypass passage is provided from the inlet opening 31*a*, 31*b*, 31*c*, 31*d*, 31*e*, 31*f*, 31g, 31*h*, 31*i* past the HME chamber 50*a*, 50*b*, 50*c*, 50*d*, 50*e*, 50*f*, 50*g*, 50*h*, 50*i* through a bypass channel 80*a*, 80*b*, 80*c*, 80*d*, 80*e*, 80*f*, 80*g*, 80*h*, 80*i* in the housing 20*a*, 20*b*, 20*c*, 20*d*, 20*e*, 20*f*, 20*g*, 20*h*, 20*i* to the outlet opening 41*a*, 41*b*, 41*c*, 41*d*, 41*e*, 41*f*, 41g, 41*h*, 41*i*, wherein the bypass channel 80*a*, 80*b*, 80*c*, 80*d*, 80*e*, 80*f*, 80*g*, 80*h*, 80*i* is blocked in the bypass mode M2 against (with respect to) the HME chamber 50*a*, 50*b*, 50*c*, 50*d*, 50*e*, 50*f*, 50*g*, 50*h*, 50*i*. In other words, the HME medium 60*a*, 60*b*, 60*c*, 60*d*, 60*e*, 60*f*, 60*g*, 60*h*, 60*i* in the HME chamber 50*a*, 50*b*, 50*c*, 50*d*, 50*e*, 50*f*, 50*g*, 50*h*, 50*i* is, in the bypass mode M2, separated at least on the patient side as well as on the ventilator side from the bypass channel 80*a*, 80*b*, 80*c*,

80*d*, 80*e*, 80*f*, 80*g*, 80*h*, 80*i*, as a result of which drug aerosol cannot come into contact with the HME medium 60*a*, 60*b*, 60*c*, 60*d*, 60*e*, 60*f*, 60*g*, 60*h*, 60*i* during the atomization of a drug.

FIGS. 1 through 5 show a first embodiment of the present invention. According to the embodiment shown in FIG. 1, the housing 20*a* has an inlet-side housing half 30*a* with the inlet opening 31*a* and an outlet-side housing half 40*a* with the outlet opening 41*a*. Further, FIG. 1 shows a switching mechanism 70*a*, with which, among other things, turning handles 45*a* and holding elements 48*a* are associated. The outlet-side housing half 40*a* can be rotated by a user in a simple manner against the inlet-side housing half 30*a* by the turning handles 45*a*. The holding elements 38*a* have a convex configuration or are configured as an arched projection at or on an outer wall section of the inlet-side housing half 30*a*. The turning handles 45*a* form a bistable holding mechanism with the holding elements 38*a*, by which holding mechanism intermediate switching states between the HME mode M1 and the bypass mode M2 can be prevented. As soon as one of the turning handles 45*a* is moved over the contour of a corresponding radial holding element 38*a*, a restoring force is generated, which acts up to the point of the greatest deflection of the turning handle 45*a*. If the turning handle 45*a* is now moved beyond this point over the contour of the holding element 38*a*, a force acts in the direction of a switchover motion. Only one of the two intermediate states, i.e., the HME mode M1 or the bypass mode M2, can thus become active, without intermediate switching states being able to be reached. Further, FIG. 1 shows an axis of rotation 21*a*, about which the outlet-side housing half 40*a* is mounted rotatably.

Figure 2:
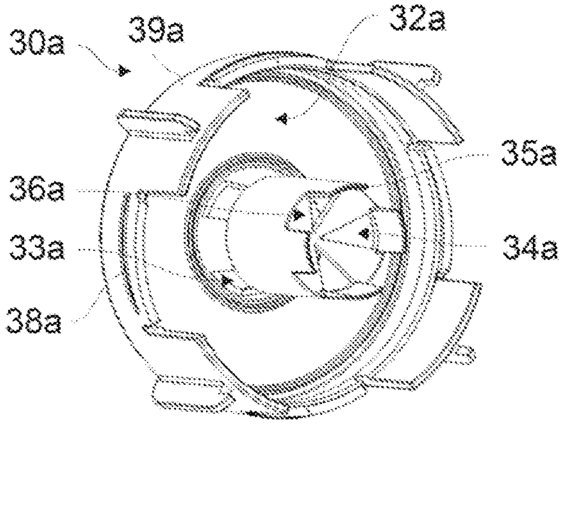
FIG. 2 is a perspective view of an inlet-side housing half of the HME device according to the first embodiment of the present invention.

FIG. 2 shows an inlet-side housing half 30*a* in detail. As is shown in FIG. 2, the inlet-side housing half 30*a* has an inner wall section 32*a*. Further, the inlet-side housing half 30*a* has first inlet holes 33*a*, second inlet holes 34*a*, inlet diaphragms 35*a* as well as inlet diaphragm passages 36*a* formed between the inlet diaphragms 35*a*.

Figure 3:
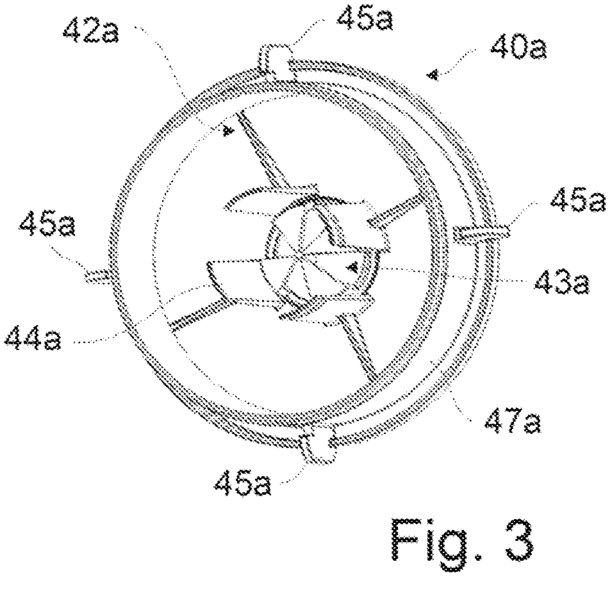
FIG. 3 is a perspective view of an outlet-side housing half of the HME device according to the first embodiment of the present invention.

FIG. 3 shows the outlet-side housing half 40*a* in detail. According to FIG. 3, the outlet-side housing half 40*a* has an inner wall section 42*a*. In addition, the outlet-side housing half 40*a* has outlet holes 43*a* and outlet diaphragms 44*a*.

Figure 4:
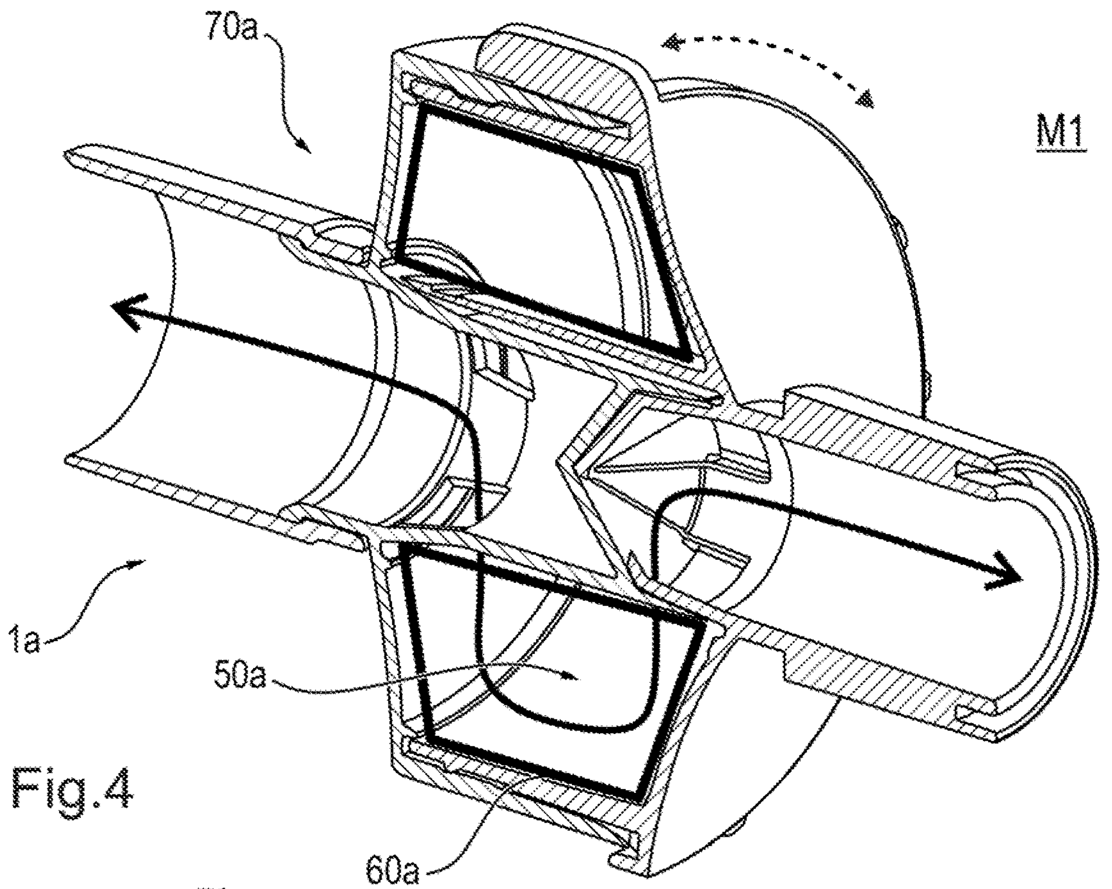
FIG. 4 is a perspective sectional view of the HME device according to the first embodiment of the present invention in an HME mode.

The HME device 1*a* is shown in the HME mode M1 in FIG. 4. The HME device is shown in the bypass mode M2 in FIG. 5. Some of the reference numbers are not shown in FIGS. 4 and 5 for the sake of greater clarity.

As is shown in FIG. 4, the HME chamber 50*a* is formed by the first inner wall section 32*a* of the inlet-side housing half 30*a* and by the second inner wall section 42*a* of the outlet-side housing half 40*a*. An inner wall section is defined here especially as a wall section or a wall surface, which wall section or wall surface is formed within an outer wall section 39*a*, 47*a* or an outer wall surface of the housing halves 30*a*, 40*a*. The inlet-side housing half 30*a* and the outlet-side housing half 40*a* are arranged rotatably relative to one another to block and open the bypass channel 80*a*. An HME fluid passage is provided in the HME mode M1 shown in FIG. 4 from the inlet opening 31*a* through the first inlet holes 33*a*, the HME chamber 50*a* and the HME medium 60*a*, the inlet diaphragm passages 36*a* to the outlet opening 41*a*. An HME fluid passage is correspondingly created at the same time from the outlet opening 41*a* through the inlet diaphragm passages 36*a*, the HME medium 60*a*, the HME chamber 50*a* and the first inlet holes 33*a* to the inlet opening 31*a*. The second inlet holes 34*a* are covered in the HME mode M1 by wall sections between the outlet holes 43*a* and the outlet holes 43*a* by wall sections between the second inlet holes 34*a* and the first inlet holes 33*a*, and the inlet diaphragm passages 36*a* are released, i.e., not covered by the outlet diaphragms 44*a*. The HME fluid passage is indicated by a double arrow in FIG. 4.

Figure 5:
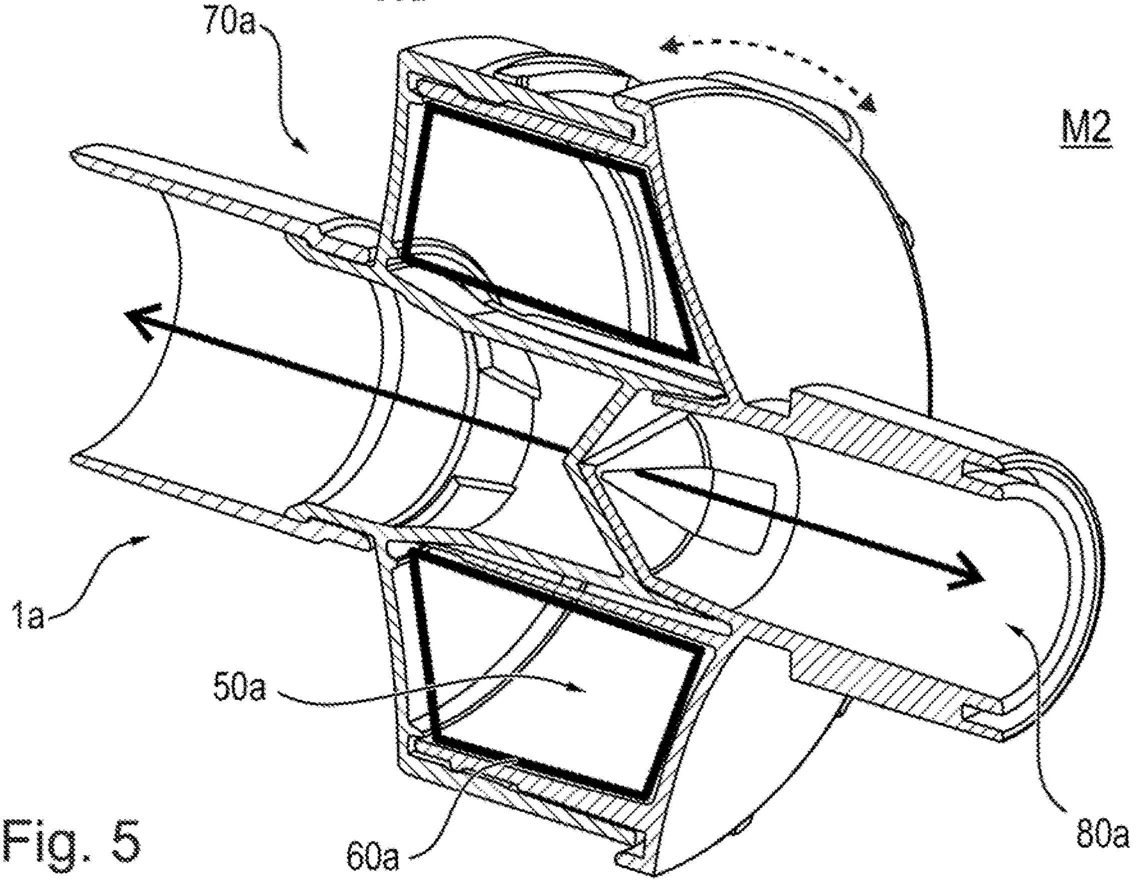
FIG. 5 is a perspective sectional view of the HME device according to the first embodiment of the present invention in a bypass mode.

A fluid bypass passage is provided in the bypass mode M2 shown in FIG. 5 from the inlet opening 31*a* past the HME chamber 50*a* as well as the HME medium 60 through the bypass channel 80*a* and also through the second inlet holes 34*a* and the outlet holes 43*a* to the outlet opening 41*a*. A fluid bypass passage is correspondingly also provided from the outlet opening 41*a* past the HME chamber 50*a* as well as the HME medium 60*a* through the bypass channel 80*a* and also through the outlet holes 43*a* and the second inlet holes 34*a* to the inlet opening 31*a*. The first inlet holes 33*a* and the inlet diaphragm passages 36*a* are covered by the outlet diaphragms 44*a* in the bypass mode M2, and the second inlet holes 34*a* are arranged flush with the outlet holes 43*a*. The fluid bypass passage is indicated by a double arrow in FIG. 5.

Figure 6:
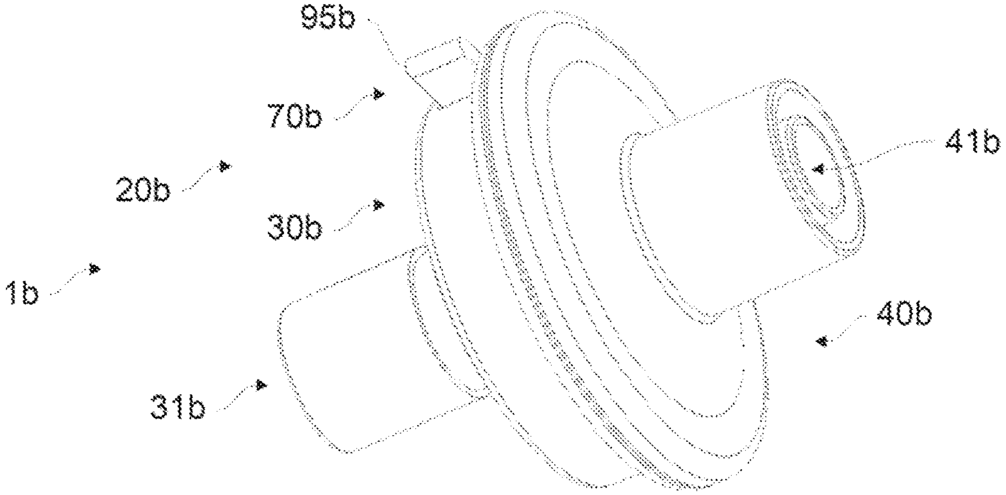
FIG. 6 is a perspective view of the HME device according to a second embodiment of the present invention.

FIGS. 6 through 9 show a second embodiment of the present invention. As is shown in FIG. 6, the housing 20*a* of the HME device 1*b* has a first housing half 30*b* with the inlet opening 31*b* and a second housing half 40*b* with the outlet opening 41*b*. Further, the HME device has a switching mechanism 70*b*, which is configured for switching over between the HME mode M1 and the bypass mode M2. Among other things, a manual actuating device 95*b* is associated with the switching mechanism 70*b*.

Figure 7:
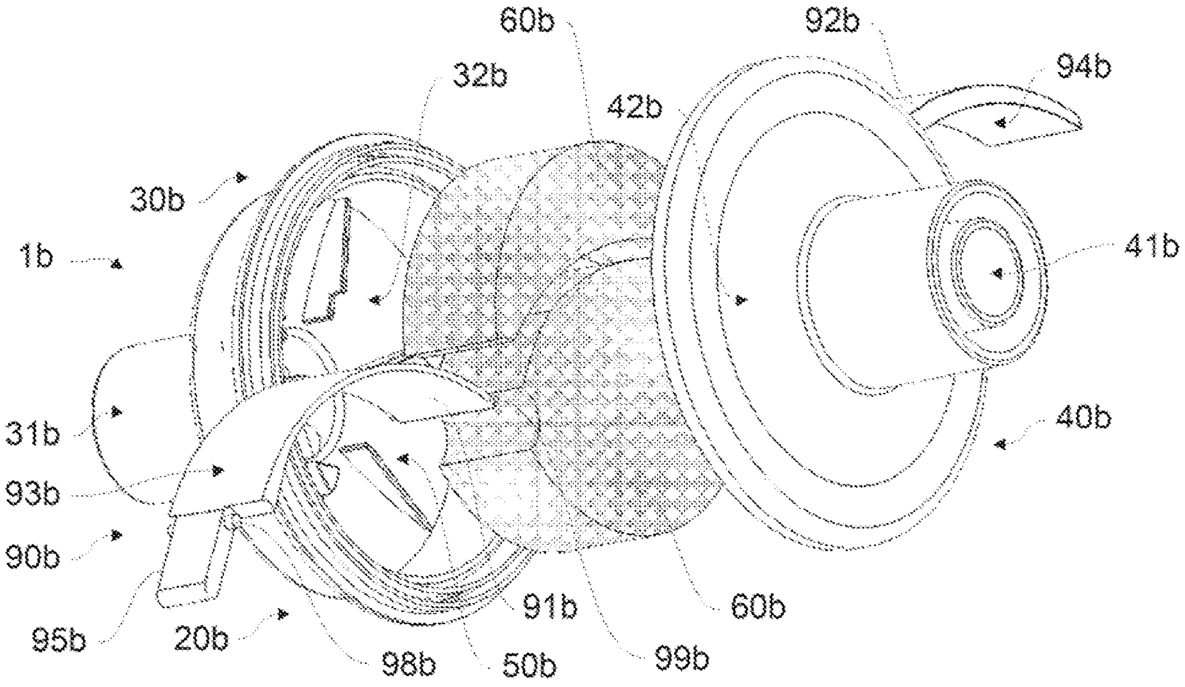
FIG. 7 is an exploded perspective view of the HME device according to the second embodiment of the present invention.

FIG. 7 shows an exploded view of the HME device 1*b* according to the second embodiment. As is seen in this view, the inlet-side housing half 30*b* has an inner wall section 32*b*. The outlet-side housing half 40*b* likewise has an inner wall section 42*b*, which is shown as being covered in FIG. 7. Further, FIG. 7 shows a sealing element 99*b* and a displacing device 90*b* for displacing the HME medium 60*b* in the HME chamber 50*b* with an outer wall section or with an outer wall surface 91*b*, 92*b*. The HME chamber 50*b* is formed here by the inner wall section 32*b* of the inlet-side housing half 30*b*, the inner wall section of the outlet-side housing half 40*b*, i.e., an inner wall section of the housing 20*b*, and by the outer wall section 91*b*, 92*b* of the displacing device 90*b* of the HME device 1*b*. The displacing device 90*b* is arranged movably for blocking a bypass channel 80*b* in the bypass mode M2 against the HME chamber 50*b*.

The displacing device 90*b* has a plate-shaped first partition section 93*b* and a plate-shaped second partition section 94*b*, an outer wall section 91*b* of the first partition section 93*b* and an outer wall section 92*b* of the second partition section corresponding to or being equivalent to the above-described outer wall section 91*b*, 92*b* of the displacing device 90*b*.

The outer wall section 91*b* or the first partition section 93*b* with the outer wall section 91*b* is elastically deformable for displacing the HME medium 60*b* and/or for blocking the bypass channel 80*b* in the bypass mode M2 against the HME chamber 50*b* and is configured movably relative to the second partition section 94*b*. For a simpler and defined motion and/of deformation of the displacing device 90*b*, this is fixed on or in the hosing 20*b*; 20*c* at four fastening points and by a first coupling element 98*b* and a second coupling element.

The manual actuating device 95*b* configured as a tumbler switch is configured here for moving or elastically deforming the displacing device 90*b* and is a monolithic component thereof.

Figure 8:
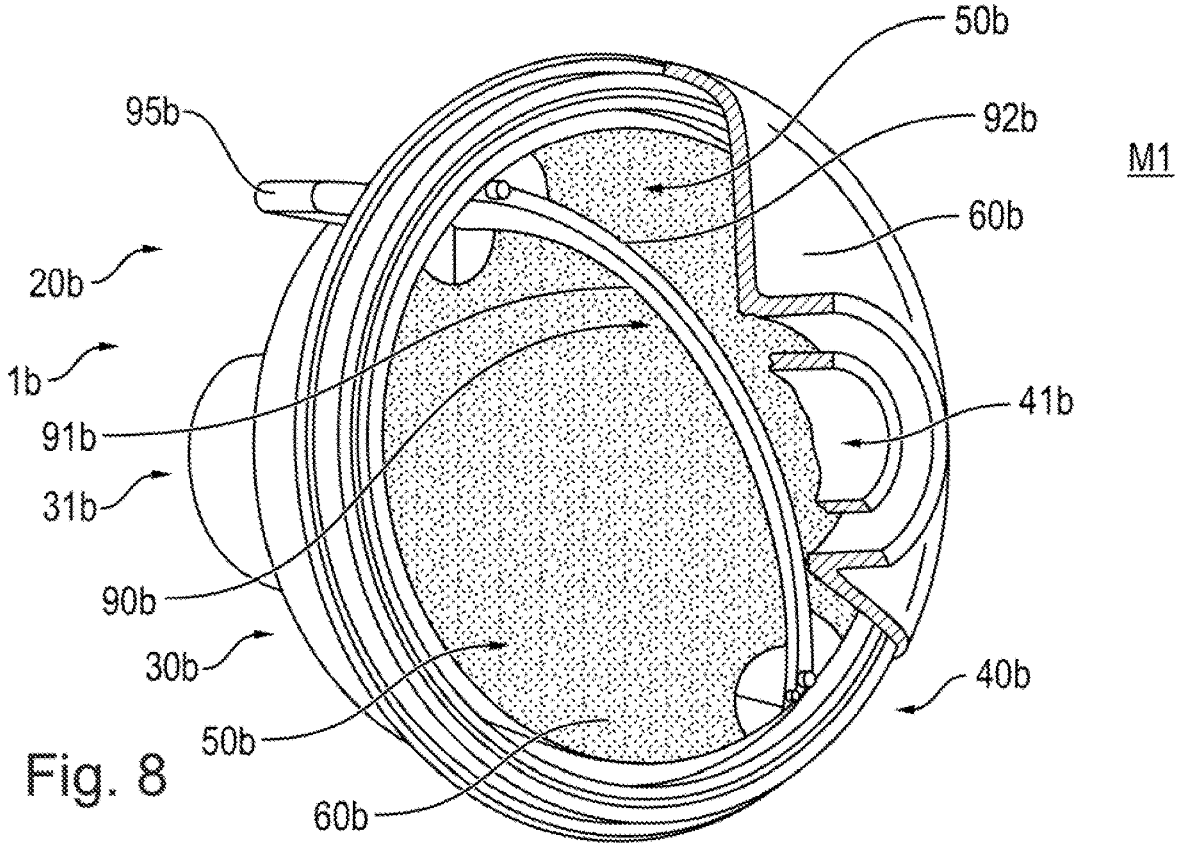
FIG. 8 is a perspective view of the HME device according to the second embodiment of the present invention in an HME mode.

FIG. 8 shows the HME device 1*b* according to the second embodiment in the HME mode M1. The first partition section 93*b* and the second partition section 94*b* are arranged in this state adjoining one another bent from a direct passage area between the inlet opening 31*b* and the outlet opening 41*b*. In other words, the two plate-shaped partition sections 93*b*, 94*b* are arranged bent in the same first direction in the HME mode M1.

Figure 9:
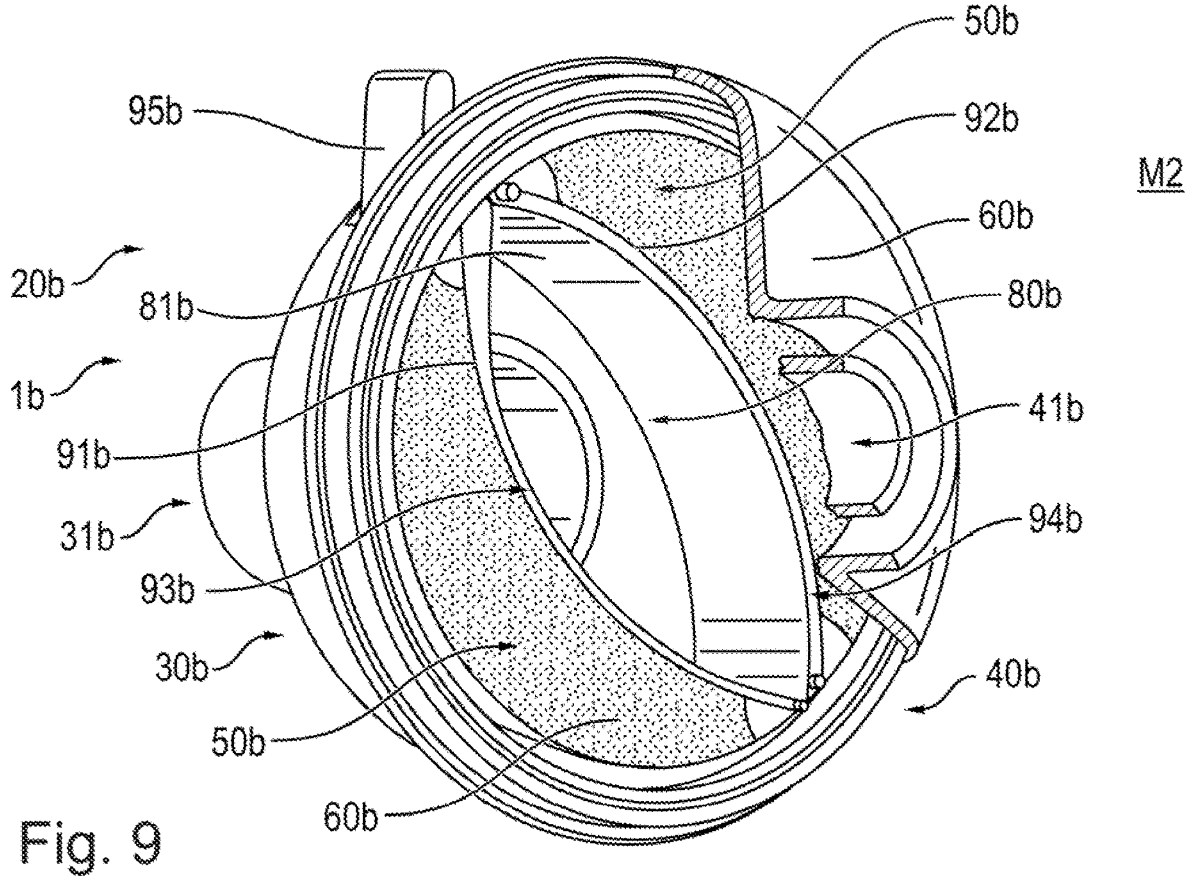
FIG. 9 is a perspective view of the HME device according to the second embodiment of the present invention in a bypass mode.

FIG. 9 shows the HME device 1*b* in the bypass mode M2. The first partition section 93*b* is elastically deformed in this state in a second direction, which is opposite the first direction, for displacing the HME medium and for blocking the bypass channel 80*b* against the HME chamber 50*b*. The first partition section 93*b* is arranged and configured here elastically deformably such that this can be deformed in a bistable manner by a residual stress into an HME end position or into a bypass end position. As is also shown in FIG. 9, the two partition sections 93*b*, 94*b* have an inner surface each, which correspond to an inner wall section 81*b* of the bypass channel 80*b*.

Figure 10:
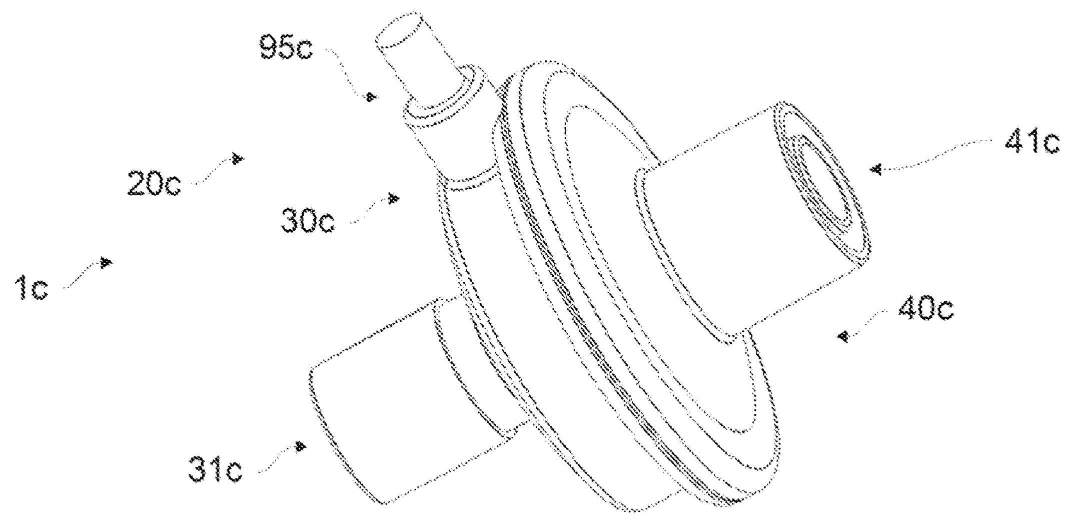
FIG. 10 is a perspective view of the HME device according to a third embodiment of the present invention.
Figure 11:
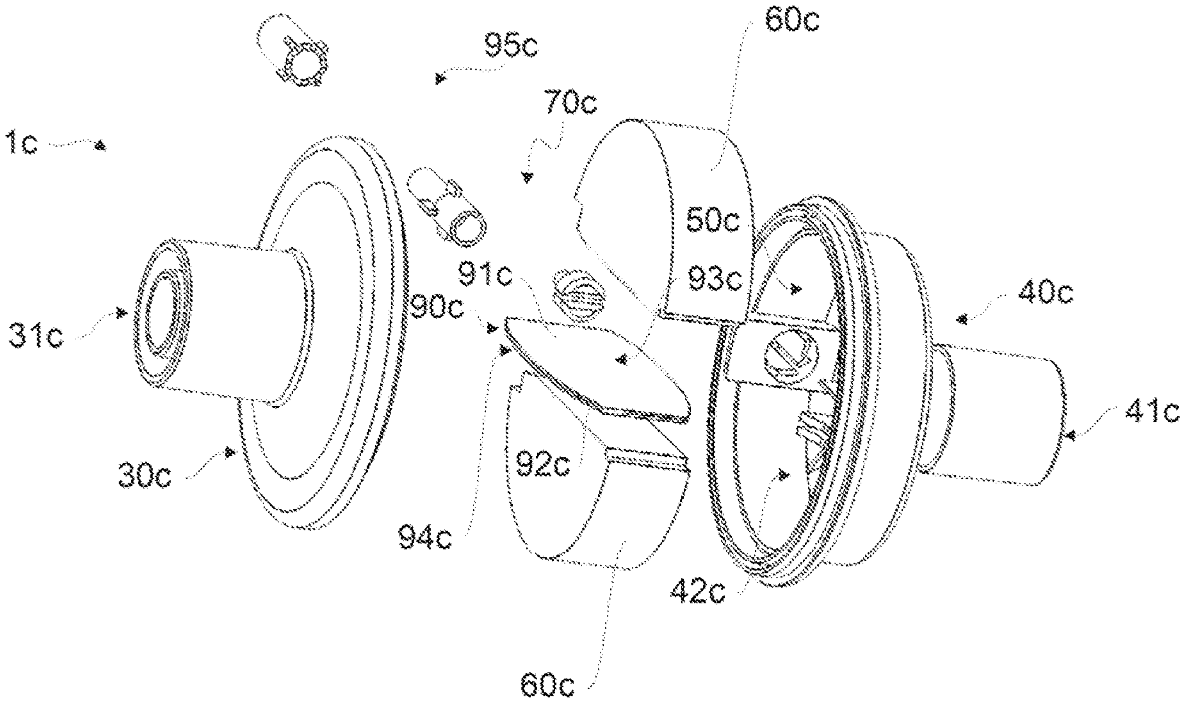
FIG. 11 is an exploded perspective view of the HME device according to the third embodiment of the present invention.
Figure 12:
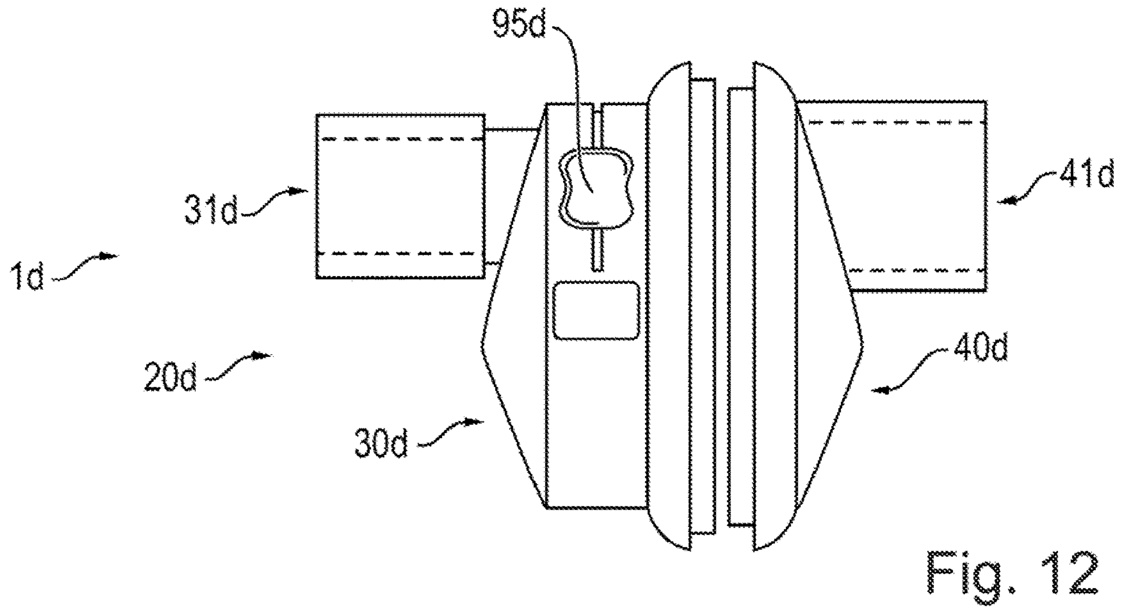
FIG. 12 is a side view of the HME device according to a fourth embodiment of the present invention.

FIGS. 10 and 11 show a third embodiment of the present invention. The housing 20*c* of the HME device 1*c* shown in FIG. 10 has an inlet-side housing half 30*c* with the inlet opening 31*c* and an outlet-side housing half 40*c* with the outlet opening 41*c*. The HME device 1*c* in FIG. 10 has, further, a manual actuating device 95*c*. The manual actuating device 95*c* has a lifting and rotating mechanical that can be actuated by pressing for moving and/or elastically deforming a displacing device 90*b*, 90*c* as is described above or, according to the third embodiment, at least one of the two plate-shaped partition sections 93*b*, 94*b* and 93*c*, 94*c*, respectively. The lifting and rotating mechanism is configured as a “clicker” or “retractable ballpoint pen mechanism” known from the state of the art and it will not therefore be explained here in more detail.

FIG. 11 shows an exploded view of the HME device 1*c* according to the third embodiment. According to FIG. 11, the HME device 1*c* has, further, a switching mechanism 70*c*, with which both the displacing device 90*c* and the manual actuating device 95*c* are associated. The displacing device 90*c* has, according to FIG. 11, an outer wall section 91*c* of a first partition section 93*c* and an outer wall section 92*c* of a second partition section 94*c*. Further, FIG. 11 shows an HME medium 60*c*, which can be arranged in an HME chamber 50*c*. The HME chamber 50*c* is formed according to the third embodiment shown in FIG. 11 by an inner wall section 42*c* of the housing 20*c* or an inner wall section of the inlet-side housing half 30*c* and by an inner wall section 42*c* of the outlet-side housing half 40*c* as well as by the outer wall section 91*c*, 92*c* of the displacing device 90*c*.

FIGS. 12 through 16 show a fourth embodiment of the present invention. The HME device 1*d* shown in FIG. 12 has an inlet-side housing half 30*d* with the inlet opening 31*d* and an outlet-side housing half 40*d* with the outlet opening 41*d*. In addition, the HME device has a manual actuating device 95*d* configured as a radial slide.

Figure 13:
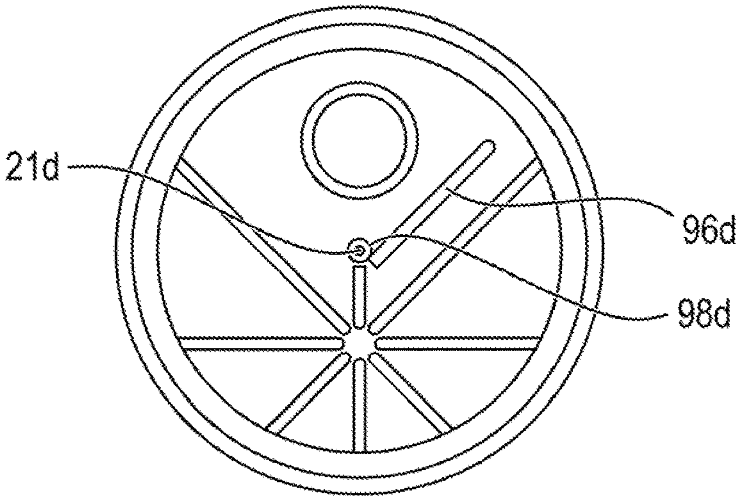
FIG. 13 is a front view of an opened HME device according to the fourth embodiment of the present invention.
Figure 14:
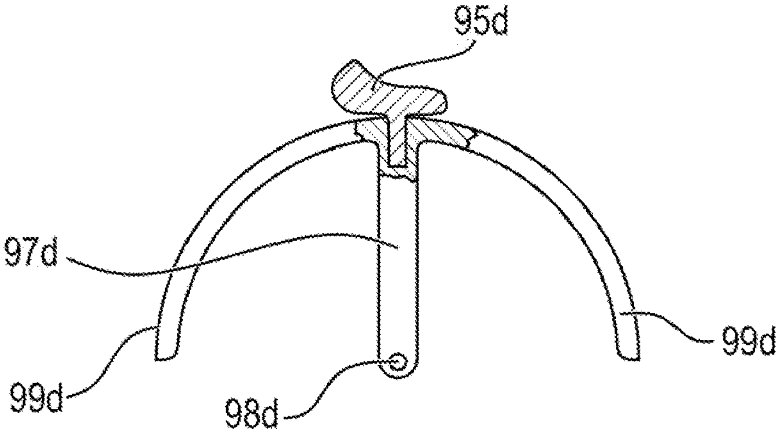
FIG. 14 is a front view of a separating device of the HME device according to the fourth embodiment of the present invention.

FIG. 13 shows a separating device 96*d* fastened in the housing 20*d*, for example, on an HME storage frame. In addition, FIG. 13 shows a coupling element 98*d*, by which an additional separating device 97*d*, pivotable about an axis of rotation 21*d*, can be arranged in the housing 20*d*. This pivotable separating device 97*d* is shown in FIG. 14. The pivotable separating device 97*d* has two arm sections, which act as a sealing element 99*d* for a sealing action between the HME chamber 50*d* and the bypass channel 80*d* in the bypass mode M2. As is also shown in FIG. 13, the manual actuating device 95*d* is permanently connected to the pivotable separating device 97*d*. More precisely, the manual actuating device 95*d* shown in FIG. 13 is arranged, in at least some sections, displaceably outside the housing 20*d* in the circumferential direction of the housing 20*d* for pivoting the movable separating device 97*d*.

Figure 15:
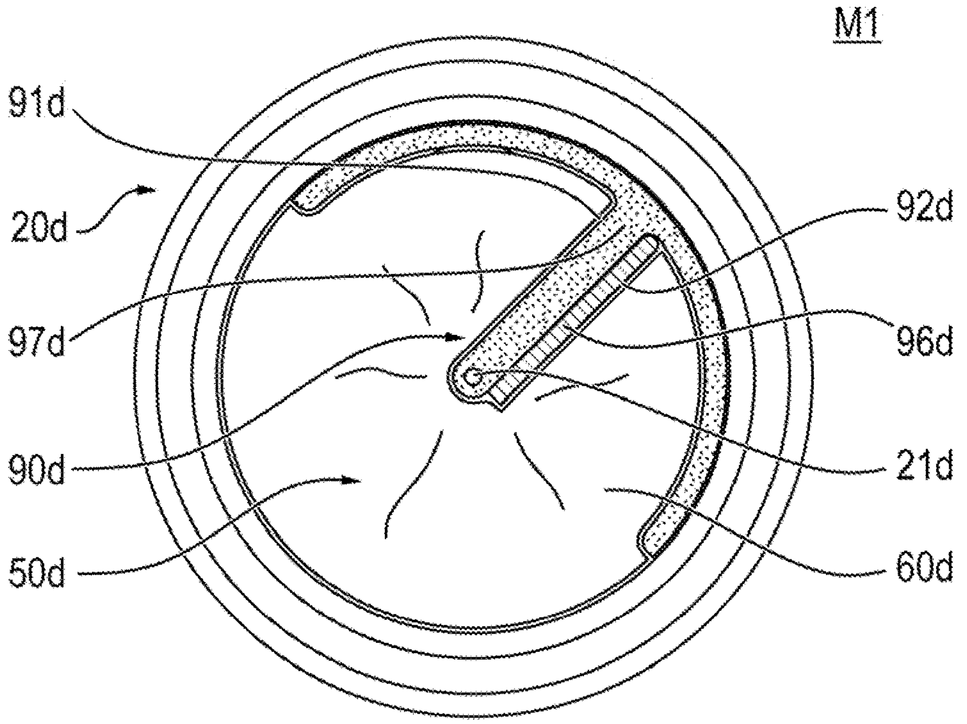
FIG. 15 is a front view of an opened HME device according to the fourth embodiment of the present invention in an HME mode.
Figure 16:
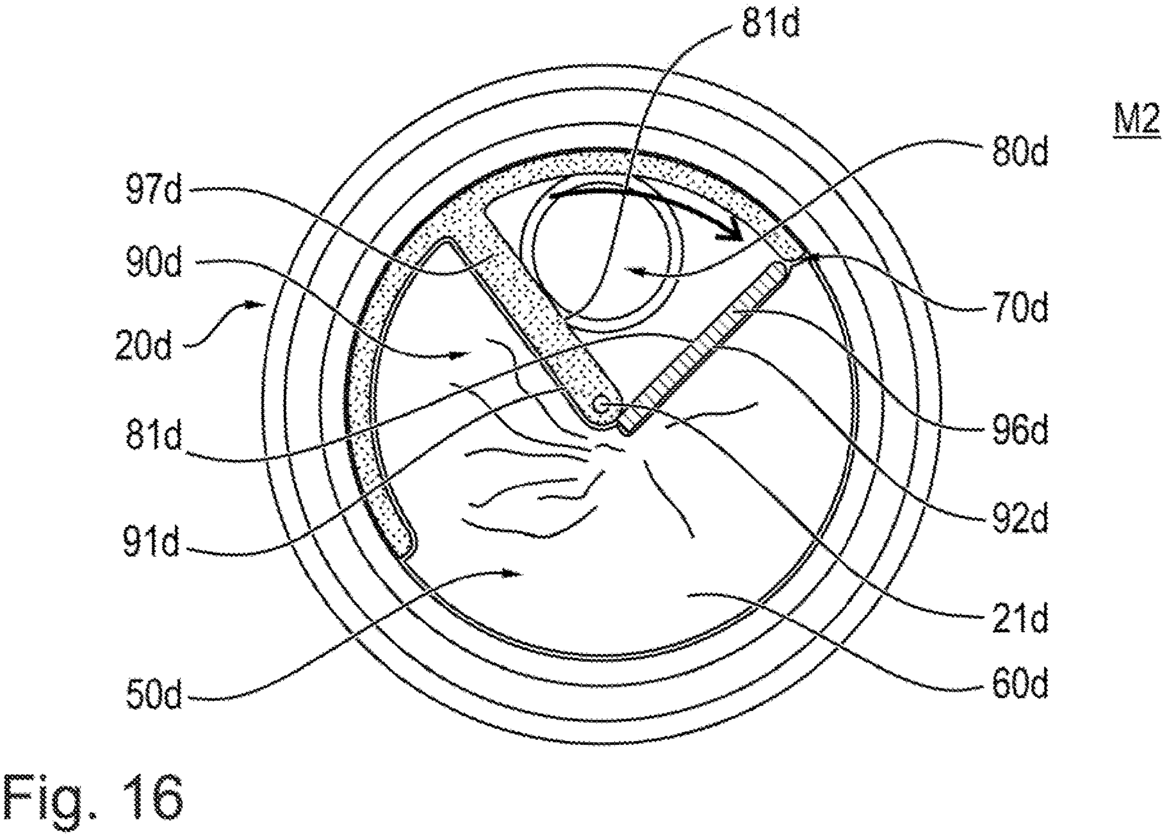
FIG. 16 is a front view of the opened HME device according to the fourth embodiment of the present invention in a bypass mode.

As is shown in FIG. 15 and FIG. 16, the HME chamber 50*d* is formed by an inner wall section of the housing 20*d* and by an outer wall section 91*d*, 92*d* of a displacing device 90*d* of the HME device 1*d* for displacing the HME medium 60*d*. The displacing device 90*d* is arranged movably for blocking the bypass channel 80*d* in the bypass mode M2 against the HME chamber 50*d*. In addition, the displacing device 90*d* has, according to the fourth embodiment, the stationary separating device 96*d* and the pivotable separating device 97*d*. Further, the stationary separating device 96*d* and the movable separating device 97*d* have each an outer wall surface and an inner wall surface, wherein the outer wall surfaces correspond to the outer wall section 91*d*, 92*d* of the displacing device 90*d* and the inner wall surfaces correspond to an inner wall section 81*d* of the bypass channel 80*d*. FIG. 15 shows the HME device 1*d* according to the fourth embodiment in an HME mode M1. The bypass channel 80*d* is closed in this state by the stationary separating device 96*d* and the pivotable separating device 97*d* being located in contact with one another or is not formed. FIG. 16 shows the HME device 1*d* according to the fourth embodiment in a bypass mode M2. A bypass channel 80*d* is provided in the bypass mode M2 with a fluid bypass passage in the HME device 1*d*. The HME device 1*d* has, further, a switching mechanism 70*d* according to FIG. 16.

Figure 17:
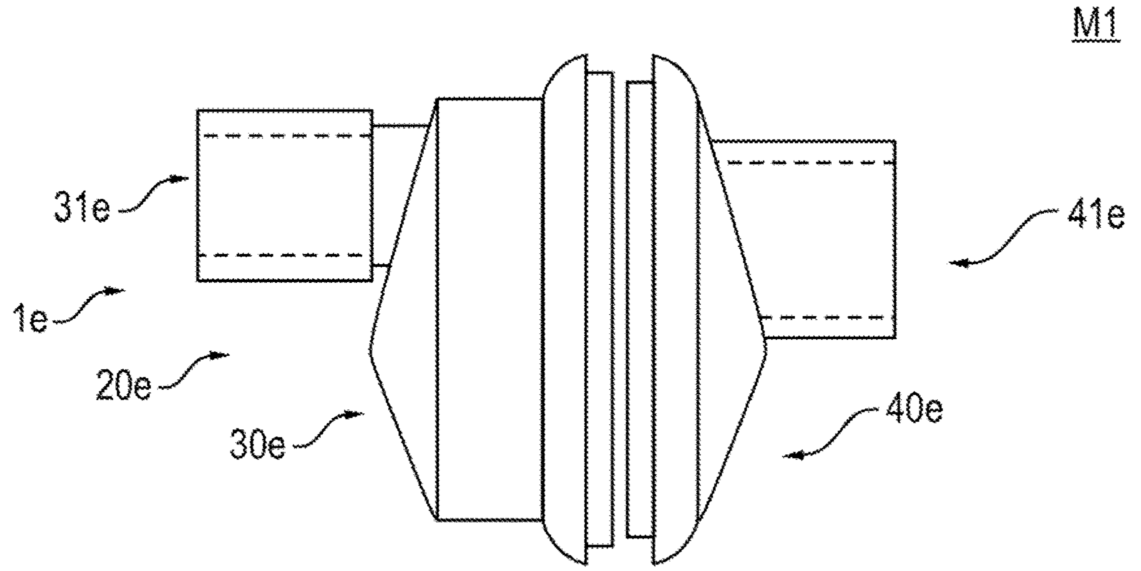
FIG. 17 is a side view of the HME device according to a fifth embodiment of the present invention in an HME mode.
Figure 18:
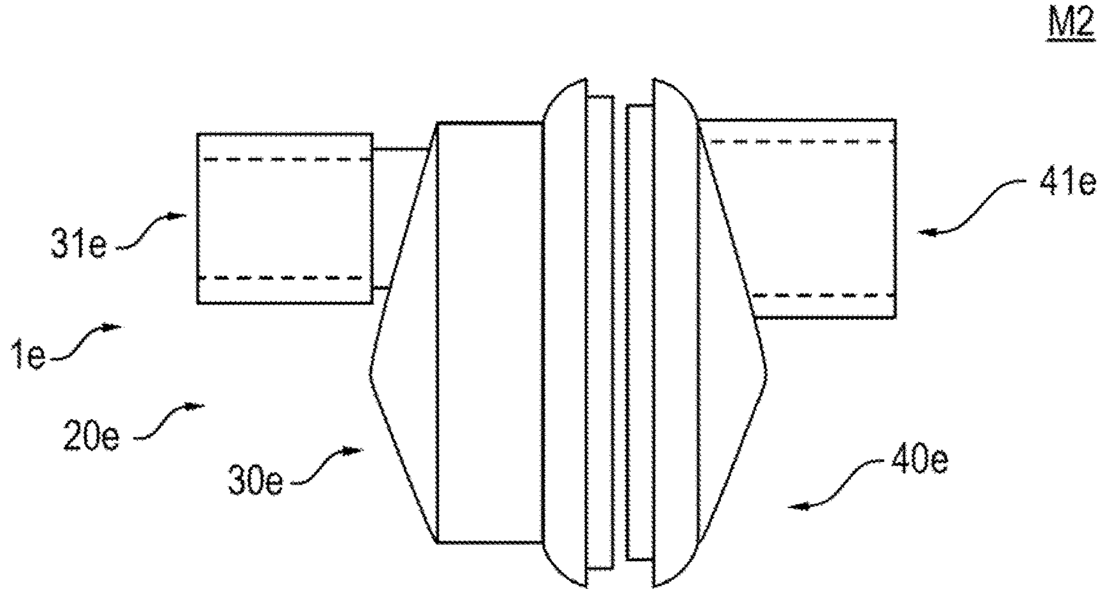
FIG. 18 is a side view of the HME device according to the fifth embodiment of the present invention in a bypass mode.

FIGS. 17 through 20 show a fifth embodiment of the present invention. The HME device 1*e* shown in FIG. 17 has an inlet-side housing half 30*e* with the inlet opening 31*e* and an outlet-side housing half 40*e* with the outlet opening 41*e*. FIG. 17 shows the HME device 1*e* in the HME mode M1. FIG. 18 shows the HME device 1*e* in the bypass mode M2. To switch over between the HME mode M1 and the bypass mode M2, the inlet-side housing half 30*a* and the outlet-side housing half 40*e* are arranged rotatably by about 30° in relation to one another for blocking and opening a bypass channel 80*e*.

Figure 19:
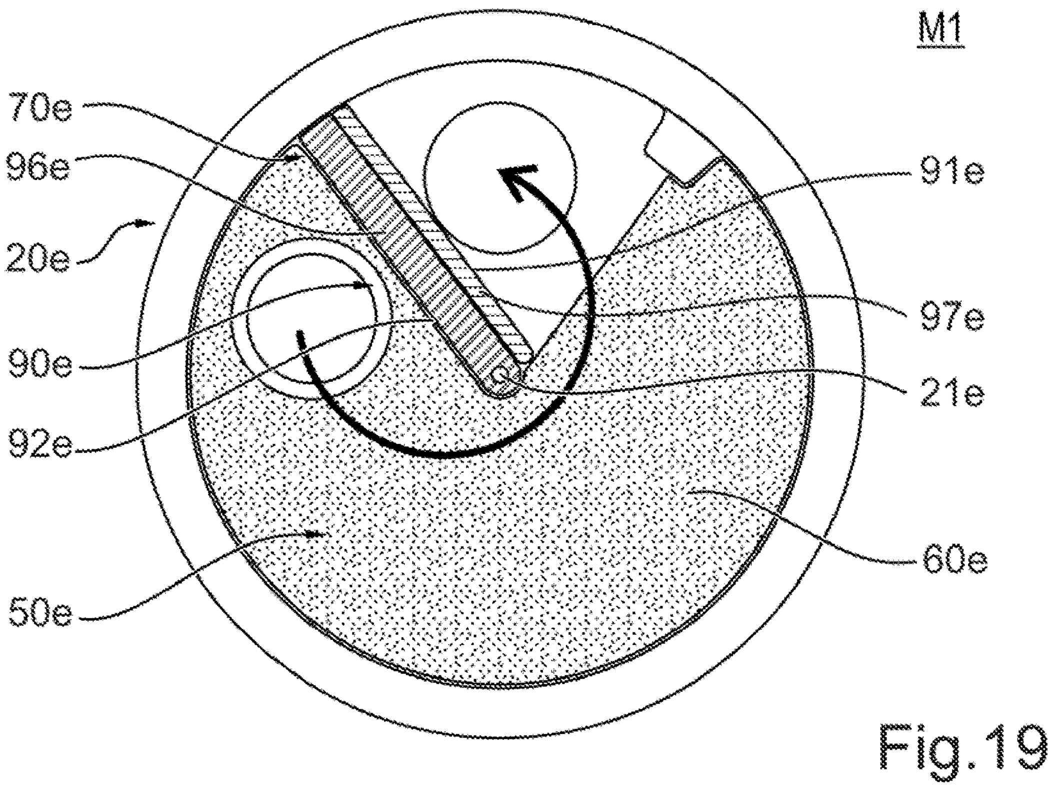
FIG. 19 is a front view of an opened HME device according to the fifth embodiment of the present invention in the HME mode.
Figure 20:
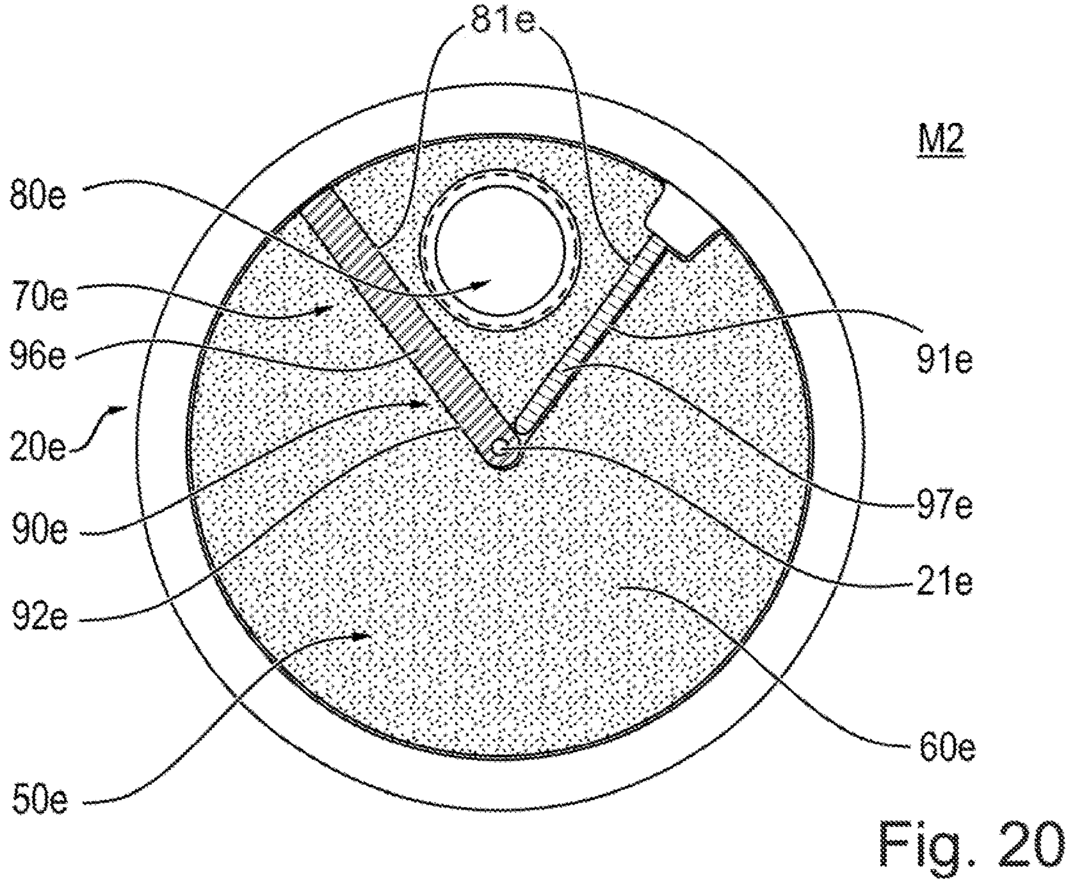
FIG. 20 is a front view of the opened HME device according to the fifth embodiment of the present invention in the bypass mode.

As is shown in FIG. 19 and FIG. 20, the HME chamber 50*e* of the HME device 1*e* is formed by a first inner wall section of the inlet-side housing half 30*e*, a second inner wall section of the outlet-side housing half 30*e* and an outer wall section 91*e*, 92*e* of a displacing device 90*e* of the HME device 1*e* for displacing the HME medium 60*e*. The displacing device 90*e* has a first separating device 96*e* and a second separating device 97*e* for blocking the bypass channel 80*e* in the bypass mode M2 against the HME chamber 50*e*, the first separating device 90*e* and the second separating device 97*e* being arranged pivotably relative to one another by rotating the housing halves 30*e*, 40*e* about the axis of rotation 21*e*. The first separating device 96*e* is in functional connection here with the inlet-side housing half 30*e* and the second separating device 97*e* is in a functional connection with the outlet-side housing half 40*e*. Further, the HME device 1*e* has, according to FIG. 19 and FIG. 20, a switching mechanism 70*e*.

The first separating device 96*e* and the second separating device 97*e* have each an outer wall surface and an inner wall surface, the outer wall surfaces corresponding to the outer wall section 91*e*, 92*e* and the inner wall surfaces corresponding to an inner wall section 81*e* of the bypass channel 80*e*.

FIGS. 21 through 24 show a sixth embodiment of the present invention. The HME device 1*f* shown in FIG. 21 has an inlet-side housing half 30*f* with the inlet opening 31*f* and an outlet-side housing half 40*f* with the outlet opening 41*f*. Further, the HME device 1*f* shown in FIG. 21 has a housing window 24*f*, through which an outer wall section or an outer wall surface of a hollow section 100*f* arranged in the housing 20*f* is exposed to the outside.

Figure 21:
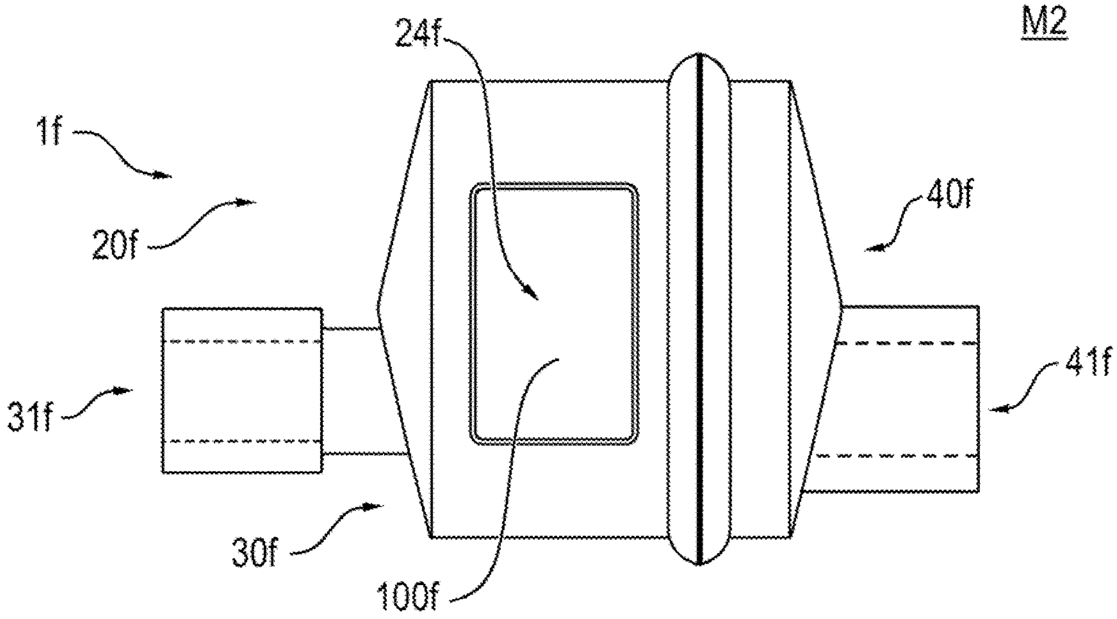
FIG. 21 is a side view of the HME device according to a sixth embodiment of the present invention in a bypass mode.
Figure 22:
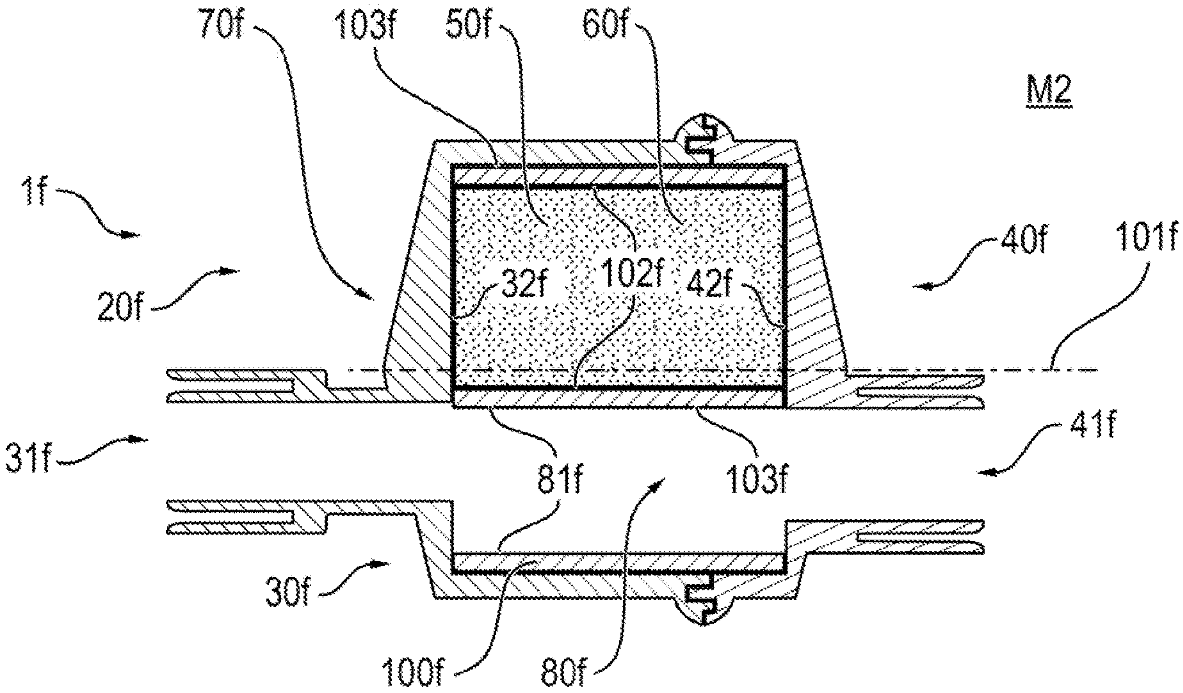
FIG. 22 is a sectional side view of the HME device according to the sixth embodiment of the present invention in the bypass mode.

FIG. 21 as well as well FIG. 22 show the HME device 1*f* in the bypass mode M2. As is shown especially in the sectional view in FIG. 22, the hollow section 100*f* is arranged rotatably about an axis of rotation 101*f* in the housing 20*f*, and an inner wall section of the HME chamber 50*f* corresponds to an inner wall section 102*f* of the hollow section 100*f*. A section of the bypass channel 80*f* can be established between a first outer wall section 103*f* of the hollow section 100*f* and a first inner wall section 22*f* of the housing 20*f*, and the first outer wall section 103*f* of the hollow section 100*f* corresponds to an inner wall section 81*f* of the bypass channel 80*f* or to this.

As it appears, further, from FIG. 22, the HME chamber 50*f* is formed by an inner wall section 102*f* of the hollow section 100*f* and by an inner wall section 32*f*, 42*f* of the housing 20*f* or of the respective housing half 30*f*, 40*f*. The HME device 1*f* has, further, according to FIG. 22, a switching mechanism 70*f*.

Figure 23:
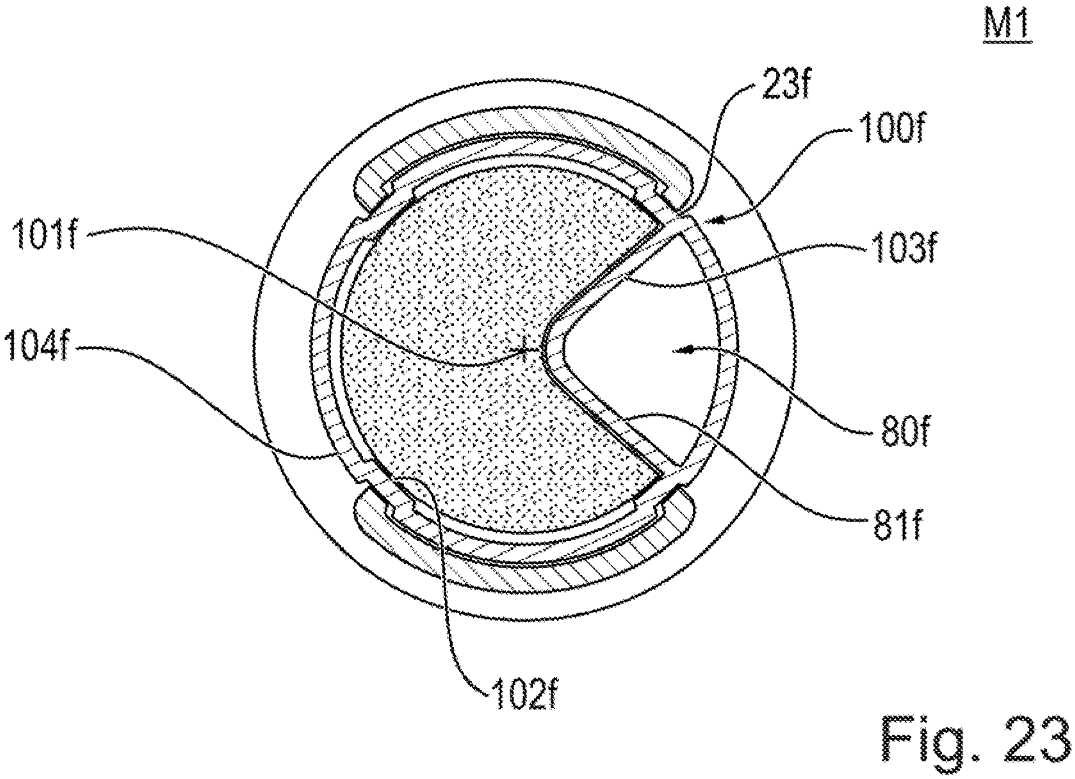
FIG. 23 is a front view of an opened HME device according to the sixth embodiment of the present invention in the HME mode.
Figure 24:
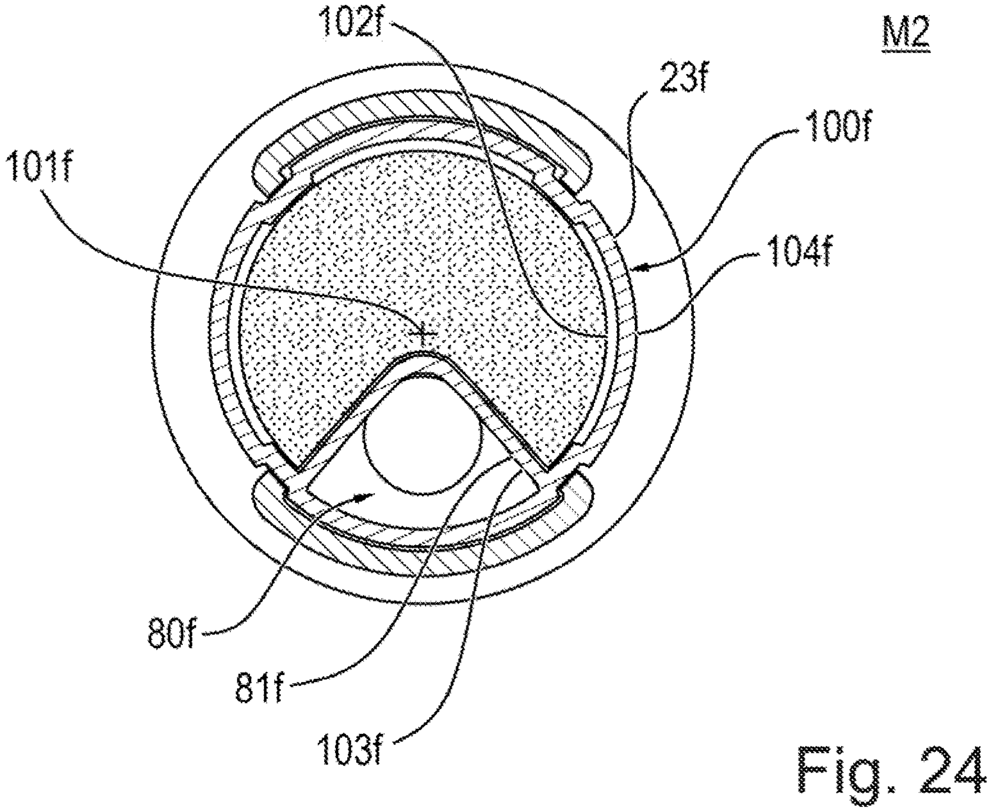
FIG. 24 is a front view of the opened HME device according to the sixth embodiment of the present invention in the bypass mode.

FIG. 23 shows the HME device if in the HME mode M1, in which the hollow section is arranged rotated in the housing 20*f* such that an HME fluid passage is formed. FIG. 24 shows the HME device if in the bypass mode M2, in which the first outer wall section 103*f* of the hollow section 100*f* corresponds to an inner wall section 81*f* of the bypass channel 80*f* or is equivalent thereto. In addition, FIG. 23 as well as FIG. 24 show that a second outer wall section 104*f* of the hollow section 100*f* is in flush-integrated contact with a second inner wall section 23*f* of the housing 20*f*.

Figure 25:
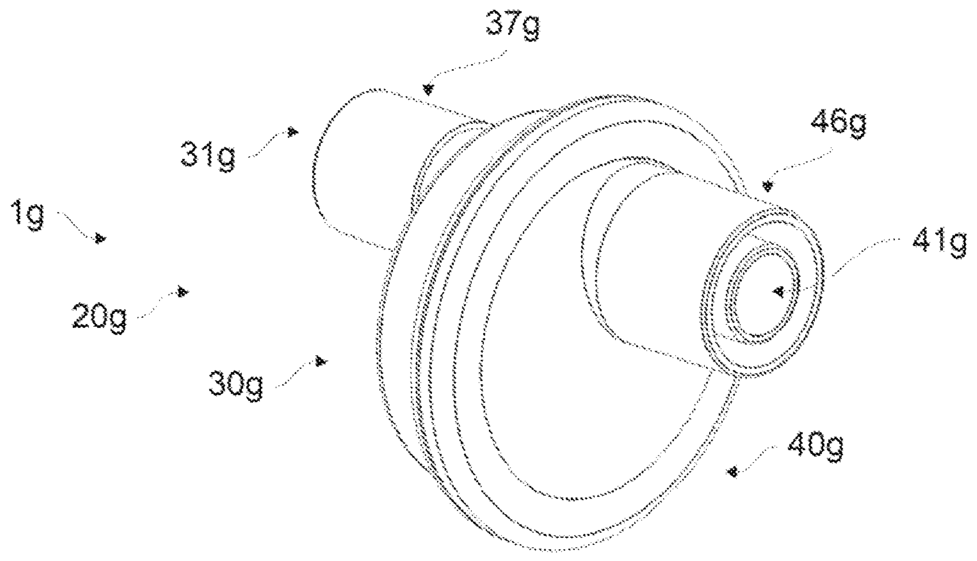
FIG. 25 is a perspective view of the HME device according to a seventh embodiment of the present invention.
Figure 26:
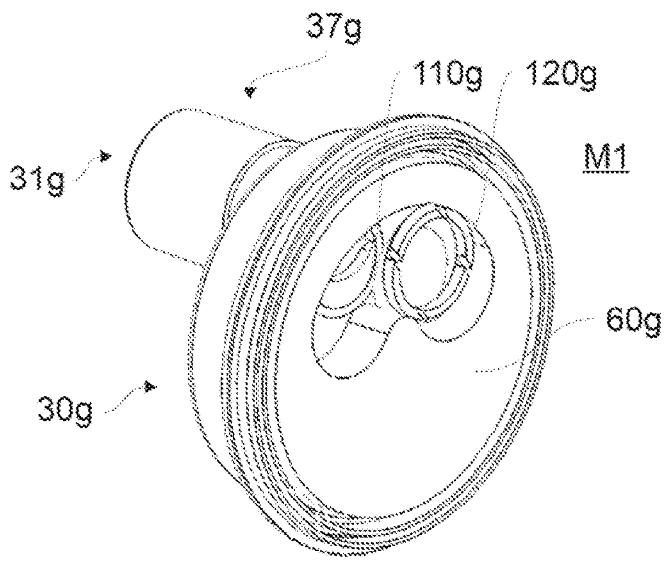
FIG. 26 is a partial perspective view of the HME device according to the seventh embodiment of the present invention.
Figure 27:
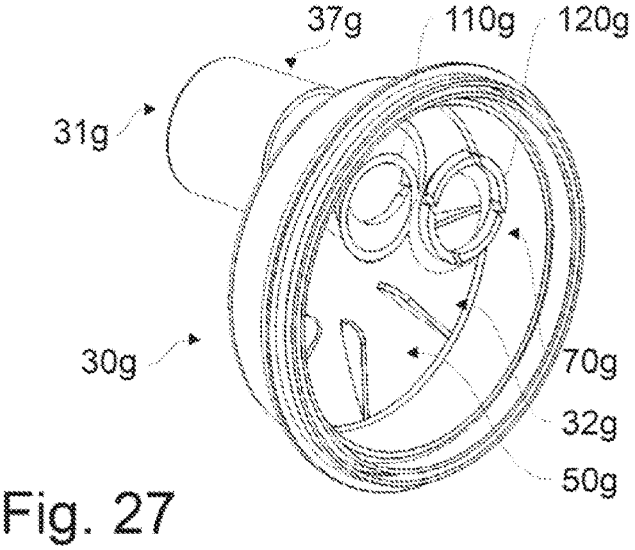
FIG. 27 is another partial perspective view of the HME device according to the seventh embodiment of the present invention.

FIGS. 25 through 27 show a seventh embodiment of the present invention. FIG. 25 shows an HME device 1*g*, in which the housing 20*g* has an inlet-side housing half 30*g* with the inlet opening 31*g* and an outlet-side housing half 40*g* with the outlet opening 41*g*. As is seen especially in FIG. 27, the HME chamber 50*g* for the HME medium 60*g* is formed by a first inner wall section 32*g* of the inlet-side housing half 30*g* and by a second inner wall section of the outlet-side housing half 40*g*. The inlet-side housing half 30*g* and the outlet-side housing half 40*g* are arranged rotated relative to one another for blocking and opening the bypass channel. Further, FIG. 27 shows a switchover mechanism 70*g*.

As is shown, further, in FIGS. 25 through 27, the housing 20*g* has a fluid inlet channel 37*g* and a fluid outlet channel 46*g*, wherein the fluid inlet channel 37*g* is connected to a first fluid switchover channel 110*g* and the fluid outlet channel 46*g* is connected to a second fluid switchover channel 120*g*, wherein the first fluid switchover channel 110*g* extends at right angles to the fluid inlet channel 37*g* and the second fluid switchover channel 120*g* extends at right angles to the fluid outlet channel 46*g*. According to the seventh embodiment, the fluid inlet channel 37*g*, the first fluid switchover channel 110*g*, the second fluid switchover channel 46*g* and the fluid outlet channel 46*g* correspond in some sections to the bypass channel in the bypass mode M2 (not shown). As can be seen in FIGS. 25 through 27, the first fluid switchover channel 110*g* and the second fluid switchover channel 120*g* are configured and can be switched over or rotated such that a flat connection can be established in the bypass mode between the ring-shaped end face of the first fluid switchover channel 110*g* and the ring-shaped end face of the second fluid switchover channel 110*g*, i.e., the first fluid switchover channel 110*g* and the second fluid switchover channel 120*g* or the respective end faces thereof adjoin each other in a fluid-tight, flush-integrated manner and provide a fluid bypass channel according to the present invention as a result.

As is shown in FIG. 26 and FIG. 27, the first fluid switchover channel 110*g* and the second fluid switchover channel 120*g* are arranged in parallel or essentially in parallel to one another in at least some sections in the HME mode M1.

As is shown by a closer scrutiny of FIG. 26, the HME medium 60*g* in the HME chamber 50*g* has a stepped passage channel 61*g*, in which the fluid outlet channel 120*g* is arranged displaceably and the fluid inlet channel 110*g* is arranged in a positive-locking manner with the HME medium 60*g* on the circumferential side.

Figure 28:
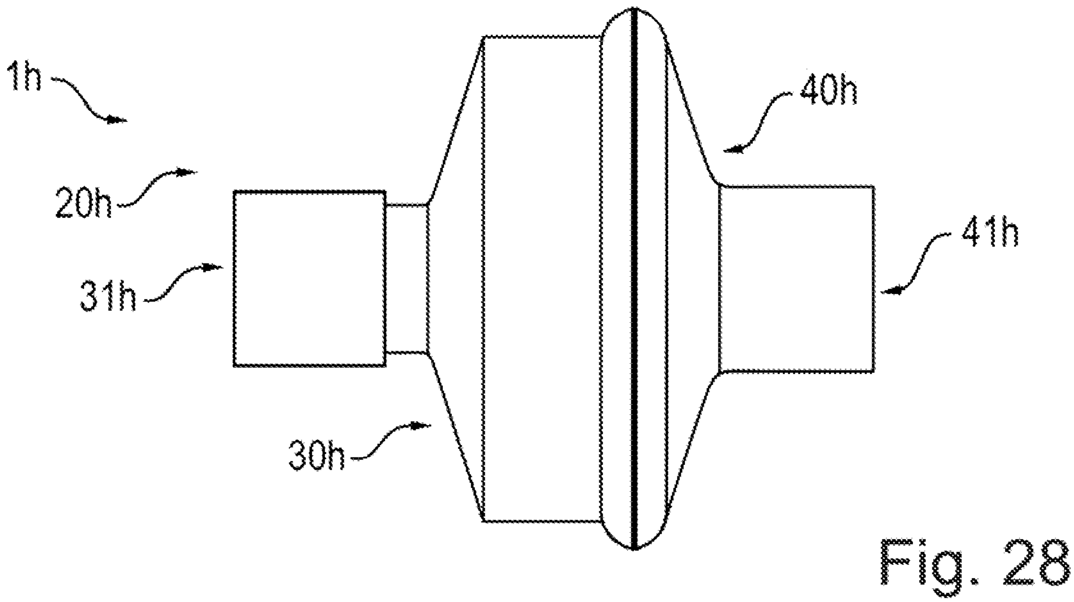
FIG. 28 is a side view of the HME device according to an eighth embodiment of the present invention in a bypass mode.

FIGS. 28 through 31 show an eighth embodiment of the present invention. FIG. 28 shows an HME device 1*h*, in which the housing 20*h* has an inlet-side housing half 30*h* with the inlet opening 31*h* and an outlet-side housing half 40*h* with the outlet opening 41*h*.

Figure 29:
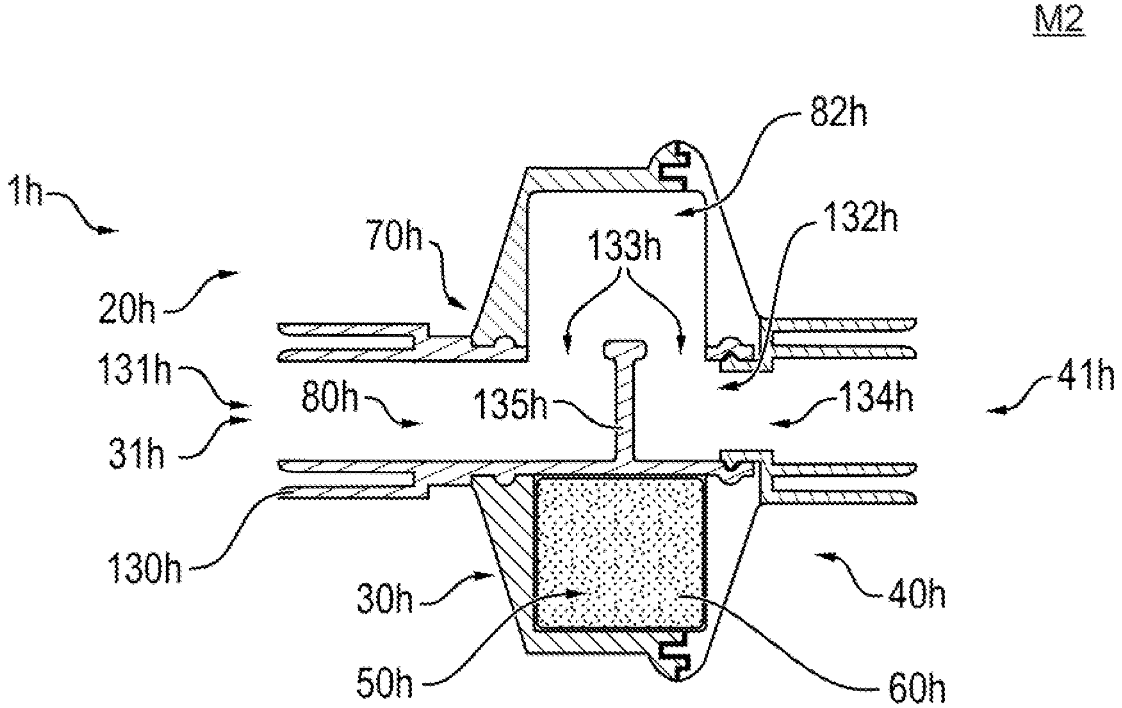
FIG. 29 is a sectional side view of the HME device according to the eighth embodiment of the present invention in the bypass mode.

FIG. 29 shows a sectional side view of the HME device 1*h* according to an eighth embodiment with the switching mechanism 70*h*. As is shown in FIG. 29, a fluid inlet channel 130*h* is arranged in the inlet-side housing half 30*h*, the fluid inlet channel 130*h* and the inlet-side housing half 30*h* being arranged rotatably in relation to one another. In addition, the inlet fluid channel 130*h* has an inlet opening 131*h*, which corresponds to the inlet opening 31*h* of the HME device 1*h* and corresponds to it, and a passage opening 132*h*. As is also shown in FIG. 29, the passage opening 132*h* is directed into the bypass channel 80*h* and a bypass channel 82*h* in the bypass mode M2. The arrangement of the bypass chamber 82*h* and of the HME chamber 80*h* are transposed in the HME mode (not shown), as a result of which the passage opening 132*h* of the non-rotated or moved fluid inlet area 130*h* is directed in this case into the HME chamber 50*h*.

In addition, the passage opening 132*h* has, according to FIG. 29, a lateral opening section 133*h* and a frontal opening section 134*h*, wherein the opening direction of the lateral opening section 133*h* is directed perpendicularly to the opening direction of the inlet opening 131*h* and of the frontal opening section 134*h*. In addition, FIG. 29 shows that the fluid inlet channel 130*h* has a wall section 135*h* that is arranged flush with the lateral opening section 133*h* in the fluid inlet channel 130*h* in parallel to the opening direction of the lateral opening section 133*h*. The wall section 135*h* has a height that corresponds to the passage level of the fluid inlet channel 130 at the location of the wall section 135*h* and corresponds to an average passage level of the fluid inlet channel 130 at the site of the wall section 135*h* and also corresponds to a mean passage level of the fluid inlet channel 130.

Figure 30:
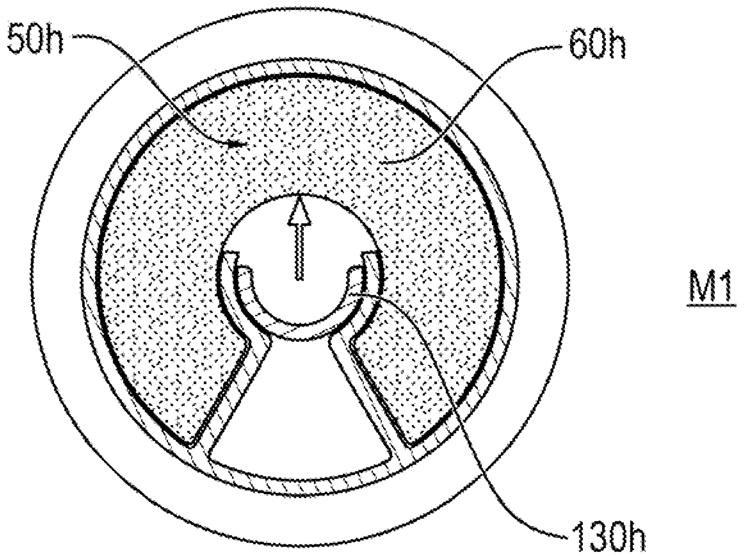
FIG. 30 is a front view of an opened HME device according to the eighth embodiment of the present invention in the HME mode.
Figure 31:
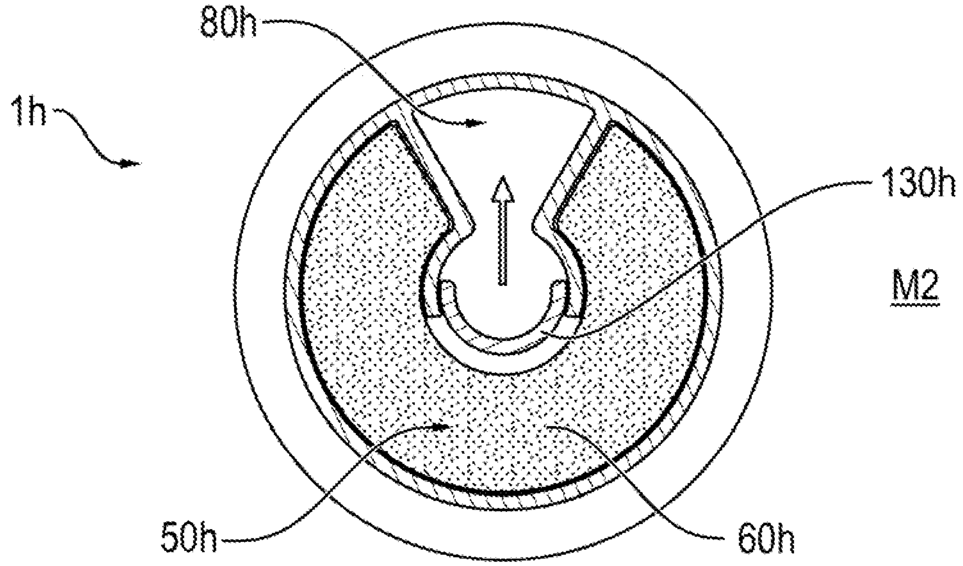
FIG. 31 is a front view of the opened HME device according to the eighth embodiment of the present invention in the bypass mode.

FIG. 30 shows the HME device 1*h* in the HME mode M1, in which the HME fluid passage is provided by the HME medium 60*h* in the HME chamber 50*h*. FIG. 31 shows the HME device 1*h* in the bypass mode M2, in which the fluid bypass passage is provided by the inlet opening 31*h* past the HME medium 60*h* in the HME chamber 50*h* to the outlet opening 41*h*.

Figure 32:
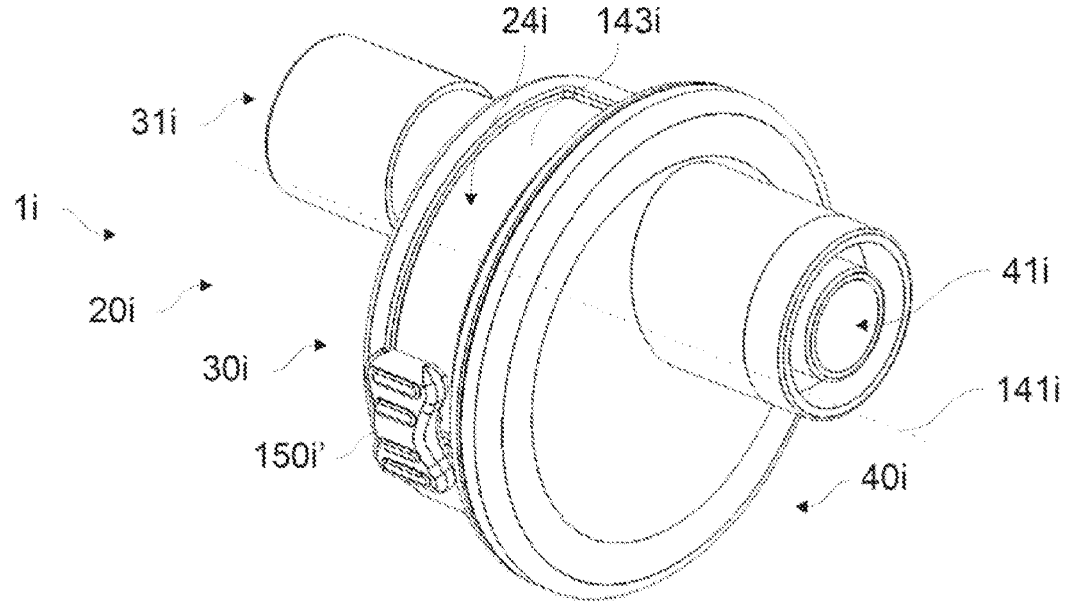
FIG. 32 is a perspective view of the HME device according to a ninth embodiment of the present invention.
Figure 33:
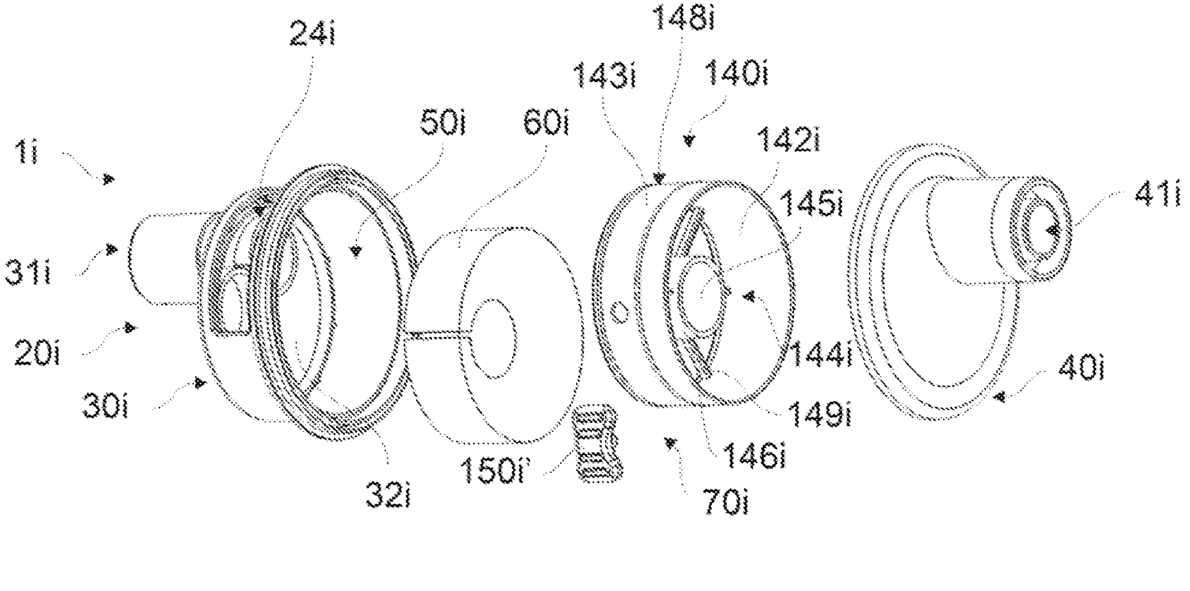
FIG. 33 is an exploded partial view of the HME device according to the ninth embodiment of the present invention.

FIGS. 32 and 33 show a ninth embodiment of the present invention. FIG. 32 shows an HME device 1*i*, in which the housing 20*i* has an inlet-side housing half 30*i* with the inlet opening 31*i* and an outlet-side housing half 40*i* with the outlet opening 41*i*. In addition, FIG. 32 shows an axis of rotation 141*i*, about which the HME storage space 140*i* is arranged rotatably. The housing 20*i* has, according to the embodiment shown in FIG. 32, a housing window 24*i*, through which an outer wall section 143*i* of the HME storage frame 140*i* is exposed to the outside. In addition, FIG. 32 shows an adjusting element 150*i*' in the form of a radially displaceable sliding switch, which element or switch is in functional connection with the HME storage frame 140*i* through the housing window 24*i*. The HME storage frame 140*i* is mounted rotatably by moving the adjusting element 150*i*' about the axis of rotation 141*i*.

FIG. 33 shows an exploded view of the HME device 1*i* according to the ninth embodiment of the present invention. FIG. 33 shows that the HME storage frame 140*i* has an outer ring section 148*i* and a storage frame passage channel 144*i* within the outer ring section 148*i*, the HME chamber 50*i* for the HME medium 60*i* being formed by an inner wall section 32*i* of the housing 20*i*, by an inner wall section 142*i* of the outer ring section 148*i* and by an outer wall section 146*i* of the storage frame passage channel 144*i*. The inner wall section 145*i* of the storage frame passage channel 142*i* corresponds to an inner wall section of the bypass channel in the bypass mode (not shown). FIG. 33 shows, in addition, that the storage frame passage channel 144*i* is held by connection struts 149*i* in the outer ring section 148*i*. The HME device 1*i* has, further, a switching mechanism 70*i* according to FIG. 33.

Figure 34:
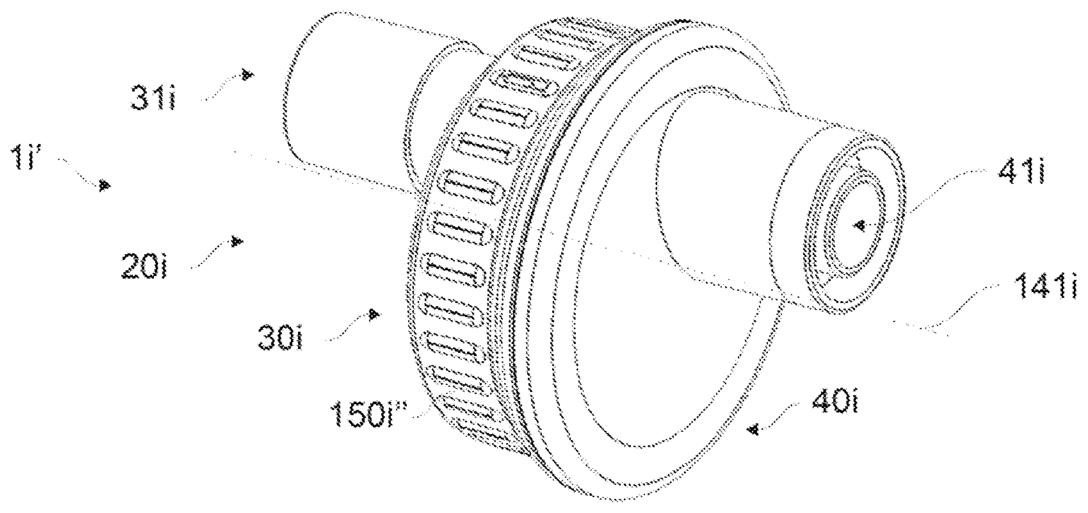
FIG. 34 is a perspective view of the HME device according to a tenth embodiment of the present invention.
Figure 35:
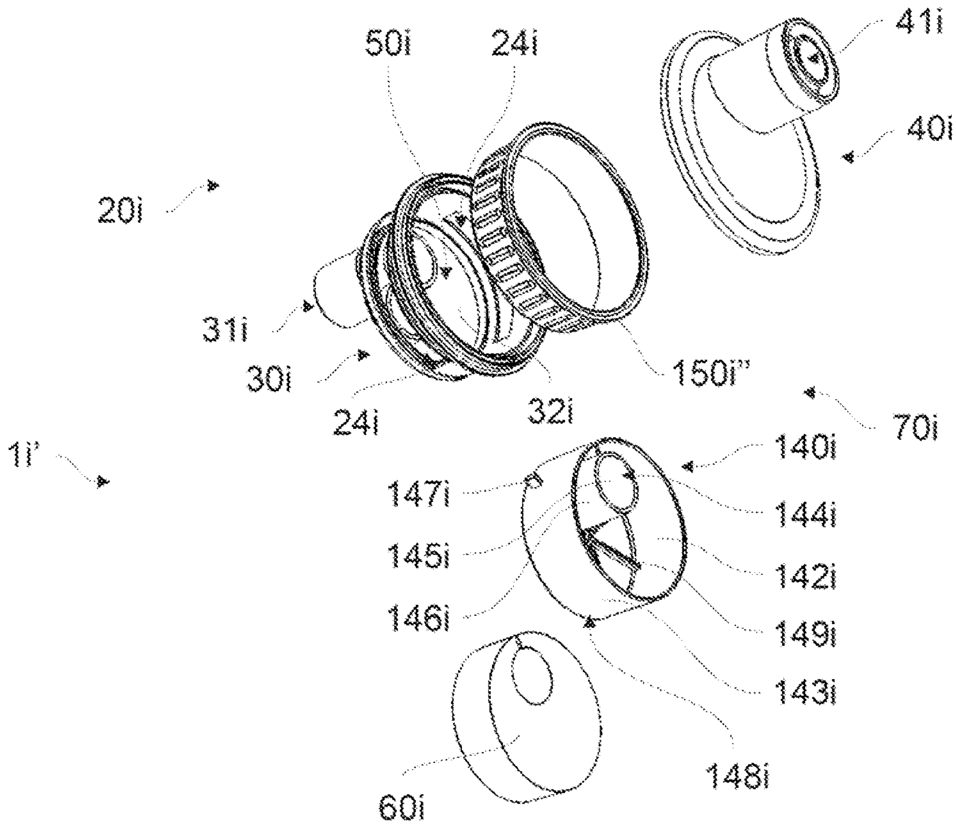
FIG. 35 is a perspective exploded view of the HME device according to the tenth embodiment of the present invention.

FIGS. 34 and 35 show an HME device 1*i*' according to a tenth embodiment of the present invention. Especially the adjusting element 150*i*" of the tenth embodiment, which shows the essential distinctive feature compared to the ninth embodiment, will be described below. The adjusting element 150*i*" is functionally connected here to the HME storage frame 140*i* via a projection 147*i* from the outer wall section 143*i* of the outer ring section 148*i* through the housing window 24*i*. As a result, a user can exert a corresponding rotary motion on the HME storage frame 140*i* by rotating the ring-shaped adjusting element 150*i*".

While specific embodiments of the invention have been shown and described in detail to illustrate the application of the principles of the invention, it will be understood that the invention may be embodied otherwise without departing from such principles.

APPENDIX: LIST OF REFERENCE CHARACTERS

| | |
|---|---|
| 1a, 1b, 1c, 1d, 1f, 1g, 1h, 1i, 1i' | HME device |
| 20a, 20b, 20c, 20d, 20e, 20f, 20g, 20h, 200i | Housing |
| 21a, 21d, 21h | Axis of rotation |
| 22f | First inner wall section |
| 23f | Second inner wall section |
| 24f, 24i | Housing window |
| 30a, 30b, 30c, 30d, 30e, 30f, 30g, 30h, 30i | Inlet-side housing half |
| 31a, 31b, 31c, 31d, 31e, 31f, 31g, 31h, 31i | Inlet opening |
| 32a, 32b, 32f, 32g, 32i | Inner wall section |
| 33a | First inlet holes |
| 34a | Second inlet holes |
| 35a | Inlet diaphragms |
| 36a | Inlet diaphragm passages |
| 37g | Fluid inlet channel |
| 38a | Holding element |
| 39a | Outer wall section |
| 40a, 40b, 40c, 40d, 40e, 40f, 430g, 40h, 40i | Outlet-side housing half |
| 41a, 41b, 41c, 41d, 41e, 41f, 41g, 41h, 41i | Outlet opening |
| 42a, 42b, 42c, 42f | Inner wall section |
| 43a | Outlet holes |
| 44a | Outlet diaphragms |

| | |
|---|---|
| 45a | Turning handle |
| 46g | Fluid outlet channel |
| 47a | Outer wall section |
| 50a, 50b, 50c, 50d, 50e, 50f, 50g, 50h, 50i | HME chamber |
| 60a, 60b, 60c, 60d, 60e, 60f, 60g, 60h, 60i | HME medium |
| 61g | Stepped passage channel |
| 70a, 70b, 70c, 70d, 70e, 70f, 70g, 70h, 70i | Switching mechanism |
| 80a, 80b, 80d, 80e, 80f, 80h | Bypass channel |
| 81b, 81d, 81e | Inner wall section |
| 82h | Bypass chamber |
| 90b, 90c, 90d, 90e | Displacing device |
| 91b, 91c, 91d, 91e | Outer wall section |
| 92b, 92c, 92d, 92e | Outer wall section |
| 93b, 93c | Partition section |
| 94b, 94c | Partition section |
| 95b, 95c, 95d | Manual actuating device |
| 96d, 96e | Separating device |
| 97d, 97e | Separating device |
| 98b, 98d | Coupling element |
| 99b, 99d | Sealing element |
| 100f | Hollow section |
| 101f | Axis of rotation |

| | |
|---|---|
| 102f | Inner wall section |
| 103f | First outer wall section |
| 104f | Second outer wall section |
| 110g | First fluid switchover channel |
| 120g | Second fluid switchover channel |
| 130h | Fluid inlet channel |
| 131h | Inlet opening |
| 132h | Passage opening |
| 133h | Lateral opening section |
| 134h | Frontal opening section |
| 135h | Wall section |
| 140i | HME storage frame |
| 141i | Axis of rotation |
| 142i | Inner wall section |
| 143i | Outer wall section |
| 144i | Storage frame passage channel |
| 145i | Inner wall section |
| 146i | Outer wall section |
| 147i | Projection |
| 148i | Outer ring section |
| 149i | Connection struts |
| 150i', 150i" | Adjusting element |

What is claimed is:

1. A heat and moisture exchanger or humidification moisture exchanger (HME) device for use in a breathing circuit of a ventilation system, the device comprising:

a housing comprising an inner housing portion, an inlet opening, an outlet opening, a bypass channel and an HME chamber arranged between the inlet opening and the outlet opening for receiving an HME medium, the inner housing portion comprising an inlet side housing half and an outlet side housing half, the inlet side housing half and the outlet side housing half being arranged radially around the bypass channel, the inlet side housing half comprising inlet side housing half inlet holes and inlet side housing half diaphragm passages, the outlet side housing half comprising outlet side housing half outlet diaphragms; and a switching mechanism configured to switch the housing between an HME mode and a bypass mode, the switching mechanism comprising the inlet side housing half and the outlet side housing half, wherein an HME fluid flow path is defined by the inlet opening, at least one of the inlet side housing half diaphragm passages, at least one of the inlet side housing half inlet holes, the HME chamber and the outlet opening in the HME mode, wherein a fluid bypass fluid flow path is defined by the inlet opening, the bypass channel and the outlet opening in the bypass mode, wherein the bypass channel is blocked from the HME chamber in the bypass mode, the outlet side housing half diaphragms releasing the inlet side housing half diaphragm passages and the inlet side housing half inlet holes in the HME mode, the outlet side housing half diaphragms blocking the inlet side housing half inlet diaphragm passages and the inlet side housing half inlet holes in the bypass mode.

2. A device in accordance with claim 1, wherein the at least one of the inlet side housing half diaphragm passages and the at least one of the inlet side housing half inlet holes are not in fluid communication with the HME chamber in the bypass mode.

3. A device in accordance with claim 1, wherein the bypass channel is arranged radially inward of the HME chamber with respect to a longitudinal axis of the housing.

4. A device in accordance with claim 1, wherein the inlet side housing half inlet holes and the inlet side housing half diaphragm passages are located radially inward of the outlet side housing half outlet diaphragms with respect to a longitudinal axis of the housing.

5. A device in accordance with claim 4, wherein the inner housing portion further comprises a first housing wall portion and a second housing wall portion, the first housing wall portion extending radially inward of the outlet side housing half outlet diaphragms, the outlet side housing half comprising outlet side housing half outlet holes, the first housing wall portion defining a portion of one of the outlet side housing half outlet holes, the second housing wall portion extending radially inward of the inlet side housing half inlet diaphragm passages, the inlet side housing half comprising second inlet holes, the second housing wall portion defining a portion of one of the second inlet holes.

6. A device in accordance with claim 5, wherein the first housing wall portion is aligned with the second housing wall portion in the bypass mode and the one of the outlet side housing half outlet holes is aligned with the one of the second inlet holes in the bypass mode.

7. A heat and moisture exchanger or humidification moisture exchanger (HME) device comprising:

a housing comprising an inner housing portion, a housing inlet opening, a housing outlet opening, a bypass channel, and an HME chamber arranged between the housing inlet opening and the housing outlet opening, the HME chamber being configured to receive an HME medium, the inner housing portion comprising an inlet side housing half and an outlet side housing half, the inlet side housing half and the outlet side housing half being arranged radially around the bypass channel, the inlet side housing half comprising inlet side housing half inlet holes and inlet side housing half diaphragm passages, the outlet side housing half comprising outlet side housing half outlet diaphragms; and a switching mechanism configured to switch the housing between a HME mode and a bypass mode, wherein the inlet opening, at least one of the inlet side housing half diaphragm passages, at least one of the inlet side housing half inlet holes, the HME chamber and the outlet opening define at least a portion of an HME fluid flow path in the HME mode, the inlet opening, the outlet opening and the bypass channel defining a bypass fluid flow path in the bypass mode, wherein the bypass channel is blocked from the HME chamber in the bypass mode, the outlet side housing half diaphragms releasing the inlet side housing half diaphragm passages and the inlet side housing half inlet holes in the HME mode, the outlet side housing half diaphragms covering the inlet side housing half inlet diaphragm passages and the inlet side housing half inlet holes in the bypass mode.

8. A device in accordance with claim 7, wherein the at least one of the inlet side housing half diaphragm passages and the at least one of the inlet side housing half diaphragm passages are not in fluid communication with the HME chamber in the bypass mode.

9. A device in accordance with claim 7, wherein the bypass channel is arranged radially inward of the HME chamber with respect to a longitudinal axis of the housing.

10. A device in accordance with claim 7, wherein the inlet side housing half inlet holes and inlet side housing half diaphragm passages are located radially inward of the outlet side housing half outlet diaphragms with respect to a longitudinal axis of the housing.

11. A device in accordance with claim 10, wherein the inner housing portion further comprises a first housing wall portion and a second housing wall portion, the first housing wall portion extending radially inward of the outlet side housing half outlet diaphragms, the outlet side housing half comprising outlet side housing half outlet holes, the first housing wall portion defining a portion of one of the outlet side housing half outlet holes, the second housing wall portion extending radially inward of the inlet side housing half inlet diaphragm passages, the inlet side housing half comprising second inlet holes, the second housing wall portion defining a portion of one of the second inlet holes.

12. A device in accordance with claim 11, wherein the first housing wall portion is aligned with the second housing wall portion in the bypass mode and the one of the outlet side housing half outlet hole is aligned with the one of the second inlet holes in the bypass mode.

13. A device in accordance with claim 12, wherein the first housing wall portion blocks the one of the second inlet holes in the HME mode and the second housing wall portion blocks the one of the outlet side housing half outlet holes in the HME mode.

14. A heat and moisture exchanger or humidification moisture exchanger (HME) device for use in a breathing circuit of a ventilation system, the device comprising: a housing comprising an inner housing portion, an inlet opening, an outlet opening, a bypass channel and an HME chamber arranged between the inlet opening and the outlet opening for receiving an HME medium, the inner housing portion comprising an inlet side housing half and an outlet side housing half, the inlet side housing half and the outlet side housing half being arranged radially around the bypass channel, the inlet side housing half comprising inlet side housing half inlet holes and inlet side housing half diaphragm passages, the outlet side housing half comprising outlet side housing half outlet diaphragms; and a switching mechanism configured to switch the housing between a HME mode housing configuration and a bypass mode housing configuration, the switching mechanism comprising the inlet side housing half and the outlet side housing half, the HME mode housing configuration comprising a HME fluid flow path, the inlet opening, at least one of the inlet side housing half inlet holes, at least one of the inlet side housing half diaphragm passages, the HME chamber and the outlet opening defining at least a portion of the HME fluid flow path, the bypass mode housing configuration comprising a bypass fluid flow path, the inlet opening, the bypass channel and the outlet opening defining the bypass fluid flow path, the bypass mode housing configuration comprising inlet side housing half inlet holes and the inlet side housing half diaphragm passages being blocked via the outlet side housing half outlet diaphragms, wherein the bypass channel is blocked from the HME chamber with the housing in the bypass mode housing configuration.

15. A device in accordance with claim 14, wherein the at least one of the inlet side housing half diaphragm passages and the at least one of the inlet side housing half inlet holes are not in fluid communication with the HME chamber in the bypass mode housing configuration.

16. A device in accordance with claim 14, wherein the bypass channel is arranged radially inward from the HME chamber.

17. A device in accordance with claim 14, wherein the inlet side housing half inlet holes and inlet side housing half diaphragm passages are located radially inward of the outlet side housing half outlet diaphragms with respect to a longitudinal axis of the housing.

18. A device in accordance with claim 17, wherein the inner housing portion further comprises a first housing wall portion and a second housing wall portion, the first housing wall portion extending radially inward of the outlet side housing half outlet diaphragms, the outlet side housing half comprising outlet side housing half outlet holes, the first housing wall portion defining a portion of one of the outlet side housing half outlet holes, the second housing wall portion extending radially inward of the inlet side housing half inlet diaphragm passages, the inlet side housing half comprising second inlet holes, the second housing wall portion defining a portion of one of the second inlet holes.

19. A device in accordance with claim 18, wherein the bypass mode configuration comprises the first housing wall portion aligned with the second housing wall portion and the one of the outlet side housing half outlet holes aligned with one of the second inlet holes.

20. A device in accordance with claim 19, wherein the HME mode housing configuration comprises the first housing wall portion blocking the one of the second inlet holes and the second housing wall portion blocking the one of the outlet side housing half outlet holes.

* * * * *